United States Patent [19]

Sum et al.

[11] Patent Number: 5,466,684

[45] Date of Patent: Nov. 14, 1995

[54] 7-(SUBSTITUTED)-9-[(SUBSTITUTED GLYCYL)AMIDO]-6-DEMETHYL-6-DEOXYTETRACYCLINES

[75] Inventors: Phaik-Eng Sum, Pomona; Ving J. Lee, Monsey, both of N.Y.; Raymond T. Testa, Cedar Grove, N.J.

[73] Assignee: American Cyanamid Company, Wayne, N.J.

[21] Appl. No.: 304,731

[22] Filed: Sep. 12, 1994

Related U.S. Application Data

[62] Division of Ser. No. 205,009, Mar. 2, 1994, Pat. No. 5,380,888, which is a division of Ser. No. 928,589, Aug. 13, 1992, Pat. No. 5,328,902.

[51] Int. Cl.$^6$ .................................................. A61K 31/65
[52] U.S. Cl. .................................................. 514/152
[58] Field of Search ........................ 514/152, 153, 514/154

[56] References Cited

U.S. PATENT DOCUMENTS

| | | | |
|---|---|---|---|
| 2,482,055 | 9/1949 | Dugger | 260/559 |
| 3,007,965 | 11/1961 | Growich | 260/559 |
| 3,043,875 | 7/1962 | Beereboom | 260/559 |
| 3,200,149 | 8/1965 | Blackwood | 260/559 |
| 3,226,436 | 12/1965 | Petisi et al. | 206/559 |
| 3,338,963 | 8/1967 | Petisi et al. | 260/559 |
| 3,341,585 | 9/1967 | Bitha et al. | 260/559 |
| 3,360,557 | 12/1967 | Shu | 260/559 |
| 3,360,561 | 12/1967 | Zambrano | 260/559 |
| 3,518,306 | 6/1970 | Martell | 260/559 |
| 5,021,407 | 6/1991 | Levy | 514/154 |

OTHER PUBLICATIONS

Levy, Antimicrobial Agents & Chemotherapy, vol. 33, No. 8, 1373–74 (Aug. 1989).

*Primary Examiner*—Johann Richter
*Assistant Examiner*—Kimberly J. Kestler
*Attorney, Agent, or Firm*—T. S. Szatkowski

[57] ABSTRACT

The invention provides compounds of the formula:

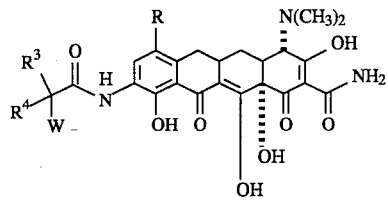

wherein R, $R^3$, $R^4$ and W are defined in the specification. These compounds are useful as antibiotic agents.

2 Claims, No Drawings

7-(SUBSTITUTED)-9-[(SUBSTITUTED GLYCYL)AMIDO]-6-DEMETHYL-6-DEOXYTETRACYCLINES

This is a divisional of application(s) Ser. No. 08/205,009, filed on Mar. 2, 1994, now U.S. Pat. No. 5,380,888; which is a divisional of application Ser. No. 07/928,589, filed on Aug. 13, 1992, now U.S. Pat. No. 5,328,902.

BACKGROUND OF THE INVENTION

FIELD OF THE INVENTION

The invention relates to novel [4S-(4alpha,12aalpha)]-4-(dimethylamino)-7-(substituted)-9-[(substituted glycyl)amido]-1,4,4a,5,5a,6,11,12a-octahydro-3,10,12,12a-tetrahydroxy-1,11-dioxo-2-naphthacenecarboxamides herein after called 7-(substituted)-9-[(substituted glycyl)amido]-6-demethyl-6-deoxytetracyclines, which exhibit antibiotic activity against a wide spectrum of organisms including organisms which are resistant to tetracyclines and are useful as antibiotic agents.

The invention also relates to novel 9-[(haloacyl)amido]-7-(substituted)-6-demethyl-6-deoxytetracycline intermediates useful for making the novel compounds of the present invention and to novel methods for producing the novel compounds and intermediate compounds.

SUMMARY OF THE INVENTION

This invention is concerned with novel 7-(substituted)-9-[(substituted glycyl)amido]-6-demethyl-6-deoxytetracyclines, represented by formula I and II, which have antibacterial activity; with methods of treating infectious diseases in warm blooded animals employing these new compounds; with pharmaceutical preparations containing these compounds; with novel intermediates compounds and processes for the production of these compounds. More particularly, this invention is concerned with compounds of formula I and II which have enhanced antibacterial activity against tetracycline resistant strains as well as a high level of activity against strains which are normally susceptible to tetracyclines.

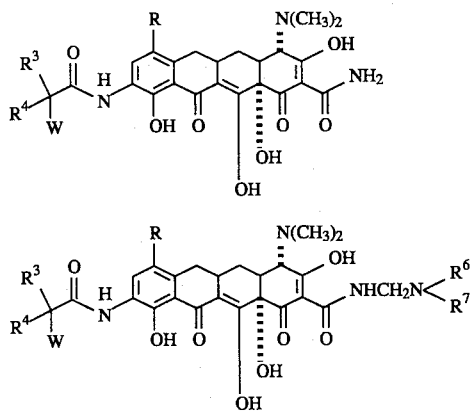

In formula I and II,

R is a halogen selected from bromine, chlorine, fluorine and iodine; or R=—NR$^1$R$^2$ and when R=—NR$^1$R$^2$ and R$^1$=hydrogen, R$^2$=methyl, ethyl, n-propyl, 1-methylethyl, n-butyl, 1-methylpropyl, 2-methylpropyl or 1,1-dimethylethyl; and when R$^1$=methyl or ethyl, R$^2$=methyl, ethyl, n-propyl, 1-methylethyl, n-butyl, 1-methylpropyl or 2-methylpropyl;

and when R$^1$=n-propyl,

R$^2$=n-propyl, 1-methylethyl, n-butyl, 1-methylpropyl or 2-methylpropyl;

and when R$^1$=1-methylethyl,

R$^2$=n-butyl, 1-methylpropyl or 2-methylpropyl; and when R$^1$=n-butyl,

R$^2$=n-butyl, 1-methylpropyl or 2-methylpropyl;

and when R$^1$=1-methylpropyl,

R$^2$=2-methylpropyl;

R$^3$ is selected from hydrogen; straight or branched (C$_4$–C$_8$)alkyl group selected from butyl, isobutyl, pentyl, hexyl, heptyl and octyl;

α-mercapto(C$_1$–C$_4$)alkyl group selected from mercaptomethyl, α-mercaptoethyl, α-mercapto-1-methylethyl and α-mercaptopropyl;

α-hydroxy(C$_1$–C$_4$)alkyl group selected from hydroxymethyl, α-hydroxyethyl, α-hydroxy-1-methylethyl and α-hydroxypropyl; carboxyl(C$_1$–C$_8$)alkyl group;

(C$_6$–C$_{10}$)aryl group selected from phenyl, α-naphthyl and β-naphthyl; substituted(C$_6$–C$_{10}$)aryl group (substitution selected from hydroxy, halogen, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino and carboxy);

(C$_7$–C$_9$)aralkyl group selected from benzyl, 1-phenylethyl, 2-phenylethyl and phenylpropyl;

substituted (C$_7$–C$_9$)aralkyl group [substitution selected from halo, (C$_1$–C$_4$)alkyl, nitro, hydroxy, amino, mono- or all-substituted (C$_1$–C$_4$)alkylamino, (C$_1$–C$_4$)alkoxy, (C$_1$–C$_4$)alkylsulfonyl, cyano and carboxy];

R$^4$ is selected from hydrogen and (C$_1$–C$_6$)alkyl selected from methyl, ethyl, propyl, isopropyl, butyl, isobutyl, pentyl and hexyl;

when R$^3$ does not equal R$^4$ the stereochemistry of the asymmetric carbon (i.e. the carbon bearing the substituent W) maybe be either the racemate (DL) or the individual enantiomers (L or D);

W is selected from hydroxylamino; (C$_7$–C$_{12}$) straight or branched alkyl monosubstituted amino group substitution selected from heptyl, octyl, nonyl, decyl, undecyl, dodecyl and the diastereomers and enantiomers of said branched alkyl monosubstituted amino group;

(C$_1$–C$_4$) straight or branched fluoroalkylamino group selected from trifluoromethyl, 2,2,2-trifluoroethyl, 3,3,3-trifluoropropyl, 3,3,3,2,2-pentafluoropropyl, 2,2-difluoropropyl, 4,4,4-trifluorobutyl and 3,3-difluorobutyl;

(C$_3$–C$_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, bicyclo[2.2.1]hept-2-yl, bicyclo[2.2.2]oct-2-yl and the diastereomers and enantiomers of said (C$_3$–C$_8$)cycloalkyl monosubstituted amino group; [(C$_4$–C$_{10}$)cycloalkyl]alkyl monosubstituted amino group substitution selected from (cyclopropyl)methyl, (cyclopropyl)ethyl, (cyclobutyl)methyl, (trans-2-methylcyclopropyl)methyl, and (cis-2-methylcyclobutyl)methyl; (C$_3$–C$_{10}$)alkenyl and alkynyl monosubstituted amino group substitution selected from allyl, 3-butenyl, 2-butenyl (cis or trans), 2-pentenyl, propynyl, 4-octenyl, 2,3-dimethyl-2-butenyl, 3-methyl-2-butenyl, 2-cyclopentenyl and 2-cyclohexenyl; ($C_6$–$C_{10}$)aryl monosubstituted amino group substitution selected from phenyl and naphthyl; ($C_7$–$C_{10}$)aralkylamino group substitution selected from benzyl, 2-phenylethyl, 1-phenylethyl, 2-(naphthyl)methyl, 1-(naphthyl)methyl and phenylpropyl; substituted ($C_6$–$C_{10}$)aryl monosubstituted amino group [substitution selected from ($C_1$–$C_5$)acyl, ($C_1$–$C_5$)acylamino, ($C_1$–$C_4$)alkyl, mono or disubstituted ($C_1$–$C_8$)alkylamino, ($C_1$–$C_4$)alkoxy, ($C_1$–$C_4$)alkoxycarbonyl, ($C_1$–$C_4$)alkylsulfonyl, amino, carboxy, cyano, halogen, hydroxy, nitro and trihalo($C_1$–$C_3$)alkyl]; straight or branched symmetrical disubstituted ($C_6$–$C_{14}$)alkylamino group substitution selected from dibutyl, diisobutyl, di-sec-butyl, dipentyl, diisopentyl, di-sec-pentyl, dihexyl, diisohexyl and di-sec-hexyl; symmetrical disubstituted ($C_6$–$C_{14}$)cycloalkylamino group substitution selected from dicyclopropyl, dicyclobutyl, dicyclopentyl, di(dicyclopropyl)methyl, dicyclohexyl and dicycloheptyl; straight or branched unsymmetrical disubstituted ($C_3$–$C_{14}$)alkylamino group wherein the total number of carbons in the substitution is more than 14; unsymmetrical disubstituted ($C_4$–$C_{14}$)cycloalkylamino group wherein the total number of carbons in the substitution is no more than 14; ($C_2$–$C_8$)azacycloalkyl and substituted ($C_2$–$C_8$)azacycloalkyl group substitution selected from 4-methylpiperidine, 4-hydroxypiperidine, 4-(hydroxymethyl)piperidine, 4-(aminomethyl)piperidine, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, 2-azabicyclo[2.2.2]oct-2-yl and the diastereomers and enantiomers of said ($C_2$–$C_8$)azacycloalkyl and substituted ($C_2$–$C_8$)azacycloalkyl group; substituted 1-azaoxacycloalkyl group substitution selected from 2-($C_1$–$C_3$)alkylmorpholinyl, 3-($C_1$–$C_3$)alkylisoxazolidinyl, tetrahydrooxazinyl and 3,4-dihydrooxazinyl; [1,n]-diazacycloalkyl and substituted [1,n]-diazacycloalkyl group selected from piperazinyl, 2-($C_1$–$C_3$)alkylpiperazinyl, 4-($C_1$–$C_3$)alkylpiperazinyl, 2,4-dimethylpiperazinyl, 4-($C_1$–$C_4$)alkoxypiperazinyl, 4-($C_6$–$C_{10}$)aryloxypiperazinyl, 4-hydroxypiperazinyl, 2,5-diazabicyclo[2.2.1]hept-2-yl, 2,5-diaza-5-methylbicyclo[2.2.1]hept-2-yl, 2,3-diaza-3-methylbicyclo[2.2.2]oct-2-yl, 2,5-diaza-5,7-dimethylbicyclo[2.2.2]oct-2-yl and the diastereomers or enantiomers of said [1,n]-diazacycloalkyl and substituted [1,n]-diazacycloalkyl group;

1-azathiacycloalkyl and substituted 1-azathiacycloalkyl group selected from thiamorpholinyl, 2-($C_1$–$C_3$)alkylthiomorpholinyl and 3-($C_3$–$C_6$)cycloalkylthiomorpholinyl; N-azolyl and substituted N-azolyl group selected from 1-imidazolyl, 2-($C_1$–$C_3$)alkyl-1-imidazolyl, 3-($C_1$–$C_3$)alkyl-1-imidazolyl, 1-pyrrolyl, 2-($C_1$–$C_3$)alkyl-1-pyrrolyl, 3-($C_1$–$C_3$)alkyl-1-pyrrolyl, 1-pyrazolyl, 3-($C_1$–$C_3$)alkyl-1-pyrazolyl, indolyl, 1-(1,2,3-triazolyl), 4-($C_1$–$C_3$)alkyl-1-(1,2,3-triazolyl), 5-($C_1$–$C_3$)alkyl-1-(1,2,3-triazolyl), 4-(1,2,4-triazolyl), 1-tetrazolyl, 2-tetrazolyl and benzimidazolyl; (heterocycle)amino group said heterocycle selected from 2- or 3-furanyl, 2- or 3-thienyl, 2-, 3- or 4-pyridyl, 2- or 5-pyridazinyl, 2-pyrazinyl, 2-(imidazolyl), (benzimidazolyl), and (benzothiazolyl) and substituted (heterocycle)amino group (substitution selected from straight or branched ($C_1$–$C_6$)alkyl); (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)methylamino group (substitution selected from straight or branched ($C_1$–$C_6$)alkyl); carboxy($C_2$–$C_4$)alkylamino group selected from aminoacetic acid, α-aminopropionic acid, β-aminopropionic acid, α-butyric acid, β-aminobutyric acid and the enantiomers of said carboxy ($C_2$–$C_4$)alkylamino group; 1,1-disubstituted hydrazino group selected from 1,1,-dimethylhydrazino, N-aminopiperidinyl, 1,1-diethylhydrazino, and N-aminopyrroli-dinyl; ($C_1$–$C_4$)alkoxyamino group substitution selected from methoxy, ethoxy, n-propoxy, 1-methylethoxy, n-butoxy, 2-methylpropoxy and 1,1-dimethylethoxy; ($C_3$–$C_8$)cycloalkoxyamino group selected from cyclopropoxy, trans-1,2-dimethylcyclopropoxy, cis-1,2-dimethylcyclopropoxy, cyclobutoxy, cyclopentoxy, cyclohexoxy, cycloheptoxy, cyclooctoxy, bicyclo[2.2.1]hept-2-yloxy, bicyclo[2.2.2]oct-2-yloxy and the diastereomers and enantiomers of said ($C_3$–$C_8$)cycloalkoxyamino group;

($C_6$–$C_{10}$)aryloxyamino group selected from phenoxyamino, 1-naphthyloxyamino and 2-naphthyloxyamino;

($C_7$–$C_{11}$)arylalkoxyamino group substitution selected from benzyloxy, 2-phenylethoxy, 1-phenylethoxy, 2-(naphthyl)methoxy, 1-(naphthyl)methoxy and phenylpropoxy;

[β or γ-($C_1$–$C_3$)acylamido]alkylamino group substitution selected from 2-(formamido)ethyl, 2-(acetamido)ethyl, 2-(propionylamido)ethyl, 2-(acetamido)propyl, 2-(formamido)propyl and the enantiomers of said [β or γ-($C_1$–$C_3$)acylamido]alkylamino group; β or γ-($C_1$–$C_3$)alkoxyalkylamino group substitution selected from 2-methoxyethyl, 2-ethoxyethyl, 2,2-diethoxyethyl, 2-methoxypropyl, 3-methoxypropyl, 3-ethoxypropyl, 3,3-diethoxypropyl and the enantiomers of said β or γ-($C_1$–$C_3$)alkoxyalkylamino group; β, γ, δ ($C_2$–$C_4$) hydroxyalkylamino group substitution selected from 2-hydroxyethyl, 2-hydroxypropyl, 3-hydroxypropyl and 4-hydroxybutyl;

or $R^3$ and W taken together are selected from —$(CH_2)_n(R^5)N$—, n=3–4, and —$CH_2CH(OH)CH_2(R^5)N$— wherein $R^5$ is selected from hydrogen and ($C_1$–$C_3$) acyl, the acyl selected from formyl, acetyl, propionyl and ($C_2$–$C_3$)haloacyl selected from chloroacetyl, bromoacetyl, trifluoroacetyl, 3,3,3-trifluoropropionyl and 2,3,3-trifluoropropionyl;

$R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

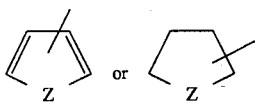

Z=N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

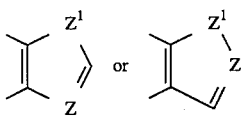

Z or $Z^1$=N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

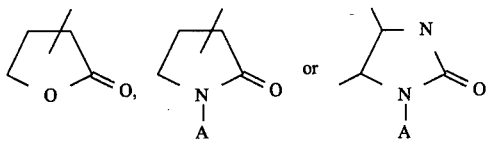

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —($CH_2$)$_n$COOR$^8$ where n=0–4 and $R^8$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, or β-naphthyl;

$R^7$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

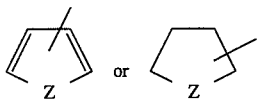

Z=N, O,S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms Z5 optionally having a benzo or pyrido ring fused thereto:

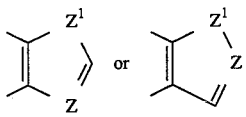

Z or $Z^1$=N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

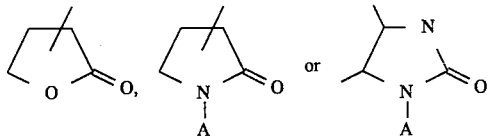

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym,triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —($CH_2$)$_n$COOR$^8$ where n=0–4 and $R^8$ is selected from hydrogen; straight or branched ($C_1$–$C_3$)alkyl selected from methyl, ethyl, n-propyl or 1-methylethyl; or ($C_6$–$C_{10}$)aryl selected from phenyl, α-naphthyl or β-naphthyl; with the proviso that $R^6$ and $R^7$ cannot both be hydrogen;

or $R^6$ and $R^7$ taken together are —($CH_2$)$_2$B($CH_2$)$_2$—, wherein B is selected from ($CH_2$)$_n$ and n=0–1, —NH, —N($C_1$–$C_3$)alkyl [straight or branched], —N($C_1$–$C_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Preferred compounds are compounds according to the above formula I and II wherein:

R is a halogen selected from bromine, chlorine, fluorine and iodine; or R=—NR$^1$R$^2$ and when R=—NR$^1$R$^2$ and R$^1$=hydrogen, R$^2$=methyl, ethyl, n-propyl, 1-methylethyl, n-butyl, 1-methylpropyl, 2-methylpropyl or 1,1-dimethylethyl; and when R$^1$=methyl or ethyl, R$^2$=methyl, ethyl, n-propyl, 1-methylethyl, n-butyl, 1-methylpropyl or 2-methylpropyl;

R$^3$ is selected from hydrogen; straight or branched (C$_4$–C$_8$)alkyl group selected from butyl, isobutyl, pentyl, hexyl, heptyl and octyl;

α-hydroxy(C$_1$–C$_4$)alkyl group selected from hydroxymethyl, α-hydroxyethyl, α-hydroxy-1-methylethyl and α-hydroxypropyl;

carboxyl(C$_1$–C$_8$)alkyl group; (C$_6$–C$_{10}$)aryl group selected from phenyl, α-naphthyl and β-naphthyl;

substituted (C$_6$–C$_{10}$)aryl group (substitution selected from hydroxy, halogen, (C$_1$–C$_4$)alkoxy, (C$_1$–C$_4$)alkoxycarbonyl and carboxy); (C$_7$–C$_9$)aralkyl group selected from benzyl, 1-phenylethyl, 2-phenylethyl and phenylpropyl;

substituted (C$_7$–C$_9$)aralkyl group [substitution selected from halo, (C$_1$–C$_4$)alkyl, (C$_1$–C$_4$)alkyl, (C$_1$–C$_4$)alkylsulfonyl, cyano and carboxy];

R$^4$ is selected from hydrogen and (C$_1$–C$_4$)alkyl selected from methyl, ethyl, propyl, isopropyl, butyl and isobutyl;

when R$^3$ does not equal R$^4$ the stereochemistry of the asymmetric carbon (i.e. the carbon bearing the substituent W) maybe be either the racemate (DL) or the individual enantiomers (L or D);

W is selected from hydroxylamino; (C$_7$–C$_{12}$) straight or branched alkyl monosubstituted amino group substitution selected from heptyl, octyl, nonyl, decyl, undecyl, dodecyl and the diastereomers and enantiomers of said branched alkyl monosubstituted amino group;

(C$_3$–C$_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, and the diastereomers and enantiomers of said (C$_3$–C$_8$)cycloalkyl monosubstituted amino group; (C$_1$–C$_4$) straight or branched fluoroalkylamino group selected from 2,2,2-trifluoroethyl, 3,3,3-trifluoropropyl, 2,2-difluoropropyl and 3,3-difluorobutyl, [(C$_4$–C$_{10}$)cycloalkyl]alkyl monosubstituted amino group substitution selected from (cyclopropyl)methyl, (cyclopropyl)ethyl, (cyclobutyl)methyl, (trans-2-methylcyclopropyl)methyl, and (cis-2-methylcyclobutyl)methyl; (C$_3$–C$_{10}$)alkenyl and alkynyl monosubstituted amino group substitution selected from allyl, 3-butenyl, 2-butenyl (cis or trans), 2-pentenyl, propynyl, 4-octenyl, 2,3-dimethyl-2-butenyl and 3-methyl-2-butenyl; (C$_6$–C$_{10}$)aryl monosubstituted amino group substitution selected from phenyl and naphthyl; (C$_7$–C$_{10}$)aralkylamino group substitution selected from benzyl, 2-phenylethyl, 1-phenylethyl, 2-(naphthyl)methyl, 1-(naphthyl)methyl and phenylpropyl; straight or branched symmetrical disubstituted (C$_6$–C$_{14}$)alkylamino group substitution selected from dibutyl, diisobutyl, di-s-butyl, dipentyl, diisopentyl and di-s-pentyl; symmetrical disubstituted (C$_6$–C$_{14}$)cycloalkylamino group substitution selected from dicyclopropyl, dicyclobutyl, dicyclopentyl and di(dicyclopropyl)methyl; straight or branched unsymmetrical disubstituted (C$_3$–C$_{14}$)alkylamino group wherein the total number of carbons in the substitution is no more than 14; unsymmetrical disubstituted (C$_4$–C$_{14}$)cycloalkylamino group wherein the total number of carbons in the substitution is no more than 14; (C$_2$–C$_8$)azacycloalkyl and substituted (C$_2$–C$_8$)azacycloalkyl group substitution selected from 4-methylpiperidine, 4-hydroxypiperidine, 4-(hydroxymethyl)piperidine, 4-(aminomethyl)piperidine, cis-3,4-dimethylpyrrolidinyl, trans-3,4-dimethylpyrrolidinyl, 2-azabicyclo [2.2.1]hept-2-yl, 7-azabicyclo [2.2.1]hept-7-yl, 2-azabicyclo[2.2.2]oct-2-yl and the diastereomers and enantiomers of said (C$_2$–C$_8$)azacycloalkyl and substituted (C$_2$–C$_8$)azacycloalkyl group; substituted 1-azaoxacycloalkyl group substitution selected from 2-(C$_1$–C$_3$)alkylmorpholinyl, 3-(C$_1$–C$_3$)alkylisoxazolidinyl and tetrahydrooxazinyl; [1,n]-diazacycloalkyl and substituted [1,n]-diazacycloalkyl group-selected from piperazinyl, 2-(C$_1$–C$_3$)alkylpiperazinyl, 4-(C$_1$–C$_3$)-alkylpiperazinyl, 2,4-dimethylpiperazinyl, 4-(C$_1$–C$_4$)-alkoxypiperazinyl, 4-(C$_6$–C$_{10}$)aryloxypiperazinyl, 4-hydroxypiperazinyl, 2,3-diaza-3-methylbicyclo [2.2.2]oct-2-yl, 2,5-diaza-5,7-dimethylbicyclo[2.2.2] oct-2-yl and the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl, 2-(C$_1$–C$_3$)alkylthiomorpholinyl and 3-(C$_3$–C$_6$)cycloalkylthiomorpholinyl; N-azolyl and substituted N-azolyl group selected from 1-imidazolyl, 1-pyrrolyl, 1-pyrazolyl, 3-(C$_1$–C$_3$)alkylpyrazolyl, indolyl, 1-(1,2,3-triazolyl), 4-(1,2,4-triazolyl), 1-tetrazolyl, 2-tetrazolyl and benzimidazolyl; (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)methylamino group (substitution selected from straight or branched (C$_1$–C$_6$)alkyl); carboxy(C$_2$–C$_4$)alkylamino group selected from aminoacetic acid, α-aminopropionic acid, β-aminopropionic acid, α-butyric acid, and β-aminobutyric acid and the enantiomers of said carboxy(C$_2$–C$_4$)alkylamino group; 1,1-disubstituted hydrazino group selected from 1,1-dimethylhydrazino, N-aminopiperidinyl and 1,1-diethylhydrazino;

(C$_1$–C$_4$)alkoxyamino group substitution selected from methoxy, ethoxy, n-propoxy, 1-methylethoxy, n-butoxy, 2-methylpropoxy and 1,1-dimethylethoxy;

(C$_3$–C$_8$)cycloalkoxyamino group selected from cyclopropoxy, trans-1,2-dimethylcyclopropoxy, cis-1,2-dimethylcyclopropoxy, cyclobutoxy, and the diastereomers and enantiomers of said (C$_3$–C$_8$)cycloalkoxyamino group;

(C$_6$–C$_{10}$)aryloxyamino group selected from phenoxyamino, 1-naphthyloxyamino and 2-naphthyloxyamino;

(C$_7$–C$_{11}$)arylalkoxyamino group substitution selected from benzyloxy, 2-phenylethoxy, 1-phenylethoxy, 2-(naphthyl)methoxy, 1-(naphthyl)methoxy and phenylpropoxy; [β or γ-(C$_1$–C$_3$)acylamido]alkylamino group substitution selected from 2-(formamido)ethyl, 2-(acetamido)ethyl, 2-(propionylamido)ethyl, 2-(acetamido)propyl, 2-(formamido)propyl and the enantiomers of said [β or γ-(C$_1$–C$_3$)acylamido]alkylamino group; β or γ-(C$_1$–C$_3$)alkoxyalkylamino group substitution selected from 2-methoxyethyl, 2-ethoxyethyl, 2,2-diethoxyethyl, 2-methoxypropyl, 3-methoxypropyl, 3-ethoxypropyl, 3,3-diethoxypropyl and the enantiomers of said β or γ-(C$_1$–C$_3$)alkoxyalkylamino group; β, γ or δ(C$_2$–C$_4$)hydroxyalkylamino group substitution selected from 2-hydroxyethyl, 3-hydroxypropyl, and 4-hydroxybutyl;

or R$^3$ and W taken together are selected from —(CH$_2$)$_n$(R$^5$)N—, n=3–4, and —CH$_2$CH(OH)CH$_2$(R$^5$)N— wherein R$^5$ selected from hydrogen and (C$_1$–C$_3$)acyl, the acyl selected from formyl, acetyl, propionyl and (C$_2$–C$_3$)haloacyl selected from chloroacetyl, bromoacetyl, trifluoroacetyl, 3,3,3-trifluoropropionyl and 2,3,3-trifluoropropionyl;

R$^6$ is selected from hydrogen; straight or branched (C$_1$–C$_3$)alkyl group selected from methyl, ethyl, n-propyl or 1-methylethyl; (C$_6$–C$_{10}$)aryl group selected from phenyl, α-naphthyl or β-naphthyl; (C$_7$–C$_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

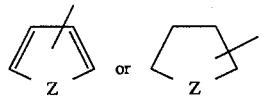

Z=N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

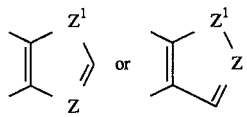

Z or Z$^1$=N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

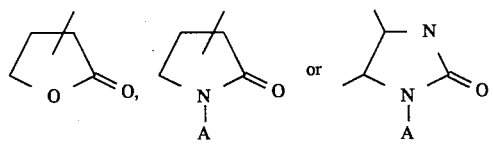

(A is selected from hydrogen; straight or branched (C$_1$–C$_4$)alkyl; C$_6$-aryl; (C$_7$–C$_9$)aralkyl group selected from benzyl, 1-phenylethyl, 2-phenylethyl or phenylpropyl)

such as γ-butyrolactam, γ-butyrolactone, imidazolidinone or N-aminoimidazolidinone; or —(CH$_2$)$_n$COOR$^8$ where n=0–4 and R$^8$ is selected from hydrogen; straight or branched (C$_1$–C$_3$)alkyl group selected from methyl, ethyl, n-propyl or 1-methylethyl; or (C$_6$–C$_{10}$)aryl group selected from phenyl, α-naphthyl, or β-naphthyl;

R$^7$ is selected from hydrogen; straight or branched (C$_1$–C$_3$)alkyl group selected from methyl, ethyl, n-propyl or 1-methylethyl; (C$_6$–C$_{10}$)aryl group selected from phenyl, α-naphthyl or β-naphthyl; (C$_7$–C$_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

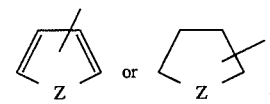

Z=N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

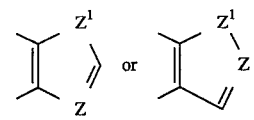

Z or Z$^1$=N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

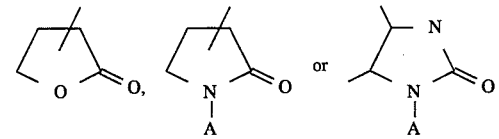

(A is selected from hydrogen; straight or branched (C$_1$–C$_4$)alkyl; C$_6$-aryl; (C$_7$–C$_9$)aralkyl group selected from benzyl, 1-phenylethyl, 2-phenylethyl or phenylpropyl)

such as γ-butyrolactam, γ-butyrolactone, imidazolidinone or N-aminoimidazolidinone; or —(CH$_2$)$_n$COOR$^8$ where n=0–4 and R$^8$ is selected from hydrogen; straight or branched (C$_1$–C$_3$)alkyl selected from methyl, ethyl, n-propyl or 1-methylethyl; or (C$_6$–C$_{10}$)aryl selected from phenyl, α-naphthyl or β-naphthyl; with the proviso that R$^6$ and R$^7$ cannot both be hydrogen;

or R$^6$ and R$^7$ taken together are —(CH$_2$)$_2$B(CH$_2$)$_2$—, wherein B is selected from (CH$_2$)$_n$ and n=0–1, —NH, —N(C$_1$–C$_3$)alkyl [straight or branched], —N($C_1$–$C_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Particularly preferred compounds are compounds according to formula I and II wherein:

R is a halogen selected from bromine, chlorine, fluorine and iodine; or R=—$NR^1R^2$ and when R=—$NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl; and when $R^1$=methyl or ethyl, $R^2$=methyl, ethyl, n-propyl, 1-methylethyl, n-butyl, 1-methylpropyl or 2-methylpropyl;

$R^3$ is selected from hydrogen; straight or branched ($C_4$–$C_6$)alkyl group selected from butyl, isobutyl, pentyl and hexyl; ($C_6$–$C_{10}$)aryl group selected from phenyl, α-naphthyl and β-naphthyl; ($C_7$–$C_9$)aralkyl group selected from benzyl, 1-phenylethyl, 2-phenylethyl and phenylpropyl;

$R^4$ is selected from hydrogen and ($C_1$–$C_3$)alkyl selected from methyl, ethyl, propyl and isopropyl;

when $R^3$ does not equal $R^4$ the stereochemistry of the asymmetric carbon (i.e. the carbon bearing the substituent W) maybe be either the racemate (DL) or the individual enantiomers (L or D);

W is selected from ($C_7$–$C_{12}$) straight or branched alkyl monosubstituted amino group substitution selected from heptyl, octyl, nonyl, decyl, undecyl, dodecyl and the diastereomers and enantiomers of said branched alkyl monosubstituted amino group; ($C_1$–$C_4$) straight or branched fluoroalkylamino group selected from 2,2,2-trifluoroethyl, 3,3,3-trifluoropropyl and 2,2-difluoropropyl; ($C_3$–$C_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl and the diastereomers and enantiomers of said ($C_3$–$C_8$)cycloalkyl monosubstituted amino group;

[($C_4$–$C_{10}$)cycloalkyl]alkyl monosubstituted amino group substitution selected from (cyclopropyl)methyl, (cyclopropyl)ethyl and (cyclobutyl)methyl; ($C_3$–$C_{10}$)alkenyl and alkynyl monosubstituted amino group substitution selected from allyl, propynyl, 3-butenyl, 2-butenyl (Cis or trans) and 2-pentenyl; ($C_7$–$C_{10}$)aralkylamino group substitution selected from benzyl, 2-phenylethyl, 1-phenylethyl, 2-(naphthyl)methyl, 1-(naphthyl)methyl and phenylpropyl; straight or branched symmetrical disubstituted ($C_6$–$C_{14}$)alkylamino group substitution selected from dibutyl, diisobutyl, di-s-butyl, and dipentyl; symmetrical disubstituted ($C_6$–$C_{14}$)cycloalkylamino group substitution selected from dicyclopropyl, dicyclobutyl, dicyclopentyl and dicyclopropylmethyl; straight or branched unsymmetrical disubstituted ($C_3$–$C_{14}$)alkylamino group wherein the total number of carbons in the substitution is no more than 14; unsymmetrical disubstituted ($C_4$–$C_{14}$)cycloalkylamino group wherein the total number of carbons in the substitution is no more than 14;

($C_2$–$C_8$)azacycloalkyl and substituted ($C_2$–$C_8$)azacycloalkyl group substitution selected from 4-methylpiperidine, 4-hydroxypiperidine, 4-(hydroxymethyl)piperidine, 4-(aminomethyl)piperidine, cis-3,4-dimethylpyrrolidinyl, trans-3,4-dimethylpyrrolidinyl, and the diastereomers and enantiomers of said ($C_2$–$C_8$)azacycloalkyl and substituted ($C_2$–$C_8$)azacycloalkyl group;

substituted 1-azaoxacycloalkyl group substitution selected from 2-($C_1$–$C_3$)alkylmorpholinyl and 3-($C_1$–$C_3$)alkylisoxazolidinyl; [1,n]-diazacycloalkyl and substituted [1,n]-diazacycloalkyl group selected from piperazinyl, 2-($C_1$–$C_3$)alkylpiperazinyl, 4-($C_1$–$C_3$)alkylpiperazinyl, 2,4-dimethylpiperazinyl, 4-hydroxypiperazinyl, and the enantiomers of said [1,n]-diazacycloalkyl and substituted [1,n]-diazacycloalkyl group;

1-azathiacycloalkyl and substituted 1-azathiacycloalkyl group selected from thiomorpholinyl and 2-($C_1$–$C_3$)alkylthiomorpholinyl;

(heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino and the substituted (heterocycle)methylamino group (substitution selected from straight or branched ($C_1$–$C_6$)alkyl); 1,1-disubstituted hydrazino group selected from 1,1-dimethylhydrazino, N-aminopiperidinyl and 1,1-diethylhydrazino;

($C_1$–$C_4$)alkoxyamino group substitution selected from methoxy, ethoxy, n-propoxy, 1-methylethoxy, n-butoxy, 2-methylpropoxy and 1,1-dimethylethoxy;

($C_7$–$C_{11}$)arylalkoxyamino group substitution selected from benzyloxy, 2-phenylethoxy, 1-phenylethoxy, 2-(naphthyl)methoxy, 1-(naphthyl)methoxy and phenylpropoxy;

[β or γ-($C_1$–$C_3$)acylamido]alkylamino group substitution selected from 2-(formamido)ethyl, 2-(acetamido)ethyl, 2-(propionylamido)ethyl, 2-(acetamido)propyl and 2-(formamido)propyl and the enantiomers of said [β or γ-($C_1$–$C_3$)acylamido]alkylamino group;

β or γ-($C_1$–$C_3$)alkoxyalkylamino group substitution selected from 2-methoxyethyl, 2-ethoxyhyl, 2,2-diethoxyethyl, 2-methoxypropyl, 3-methoxyopyl, 3-ethoxypropyl and 3,3-diethoxypropyl and the enantiomers of said β or γ-($C_1$–$C_3$)alkoxyalkyl-amino group; β, γ, or δ($C_2$–$C_4$)hydroxyalkylamino group selected from 3-hydroxypropyl and 4-hydroxybutyl;

or $R^3$ and W taken together are selected from —$(CH_2)_n)R^5)N$—, n=3–4, and —$CH_2CH(OH)CH_2(R^5)N$— wherein $R^5$ is selected from hydrogen and ($C_1$–$C_3$)acyl, the acyl selected from formyl, acetyl, propionyl and ($C_2$–$C_3$)haloacyl selected from trifluoroacetyl, 3,3,3-trifluoropropionyl and 2,3,3-trifluoropropionyl;

$R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

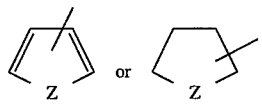

Z=N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

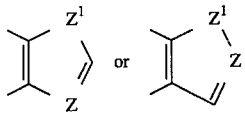

Z or $Z^1$=N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl; or —$(CH_2)_n$COOR$^8$ where n=0–4 and $R^8$ is selected from hydrogen; straight or branched $(C_1$–$C_3)$alkyl group selected from methyl, ethyl, n-propyl or 1-methylethyl; or $(C_6$–$C_{10})$aryl group selected from phenyl, α-naphthyl, or β-naphthyl;

$R^7$ is selected from hydrogen; straight or branched $(C_1$–$C_3)$alkyl group selected from methyl, ethyl, n-propyl or 1-methylethyl; $(C_6$–$C_{10})$aryl group selected from phenyl, α-naphthyl or β-naphthyl; $(C_7$–$C_9)$aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

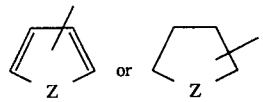

Z=N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

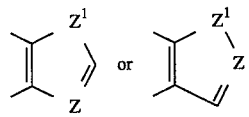

Z or $Z^1$=N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl; or —$(CH_2)_n$COOR$^8$ where n=0–4 and $R^8$ is selected from hydrogen; straight or branched $(C_1$–$C_3)$alkyl selected from methyl, ethyl, n-propyl or 1-methylethyl; or $(C_6$–$C_{10})$aryl selected from phenyl, α-naphthyl or β-naphthyl; with the proviso that $R^6$ and $R^7$ cannot both be hydrogen;

or $R^6$ and $R^7$ taken together are —$(CH_2)_2$B$(CH_2)_2$—, wherein B is selected from $(CH_2)_n$ and n=0–1, —NH, —N$(C_1$–$C_3)$alkyl [straight or branched], —N$(C_1$–$C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Compounds of special interest are compound according to formula I and II wherein:

R is a halogen selected from bromine, chlorine and iodine; or R=—NR$^1$R$^2$ and when R=—NR$^1$R$^2$ and R$^1$=methyl or ethyl, R$^2$=methyl or ethyl, R$^3$ is selected from hydrogen;

R$^4$ is selected from hydrogen and $(C_1$–$C_2)$alkyl selected from methyl and ethyl;

when R$^3$ does not equal R$^4$ the stereochemistry of the asymmetric carbon (i.e. the carbon bearing the substituent W) maybe be either the racemate (DL) or the individual enantiomers (L or D);

W is selected from $(C_7$–$C_{12})$ straight or branched alkyl monosubstituted amino group substitution selected from heptyl, octyl, nonyl, decyl, undecyl, dodecyl and the diastereomers and enantiomers of said branched alkyl monosubstituted amino group; $(C_2)$fluoroalkylamino group selected from 2,2,2-trifluoroethyl and 3,3,3-trifluoropropyl;

$(C_3$–$C_8)$cycloalkyl monosubstituted amino group substitution selected from cyclopropyl, cyclobutyl, cyclopentyl, cyclohexyl and the diastereomers and enantiomers of said $(C_3$–$C_8)$cycloalkyl monosubstituted amino group; $[(C_4$–$C_5)$cycloalkyl]alkyl monosubstituted amino group substitution selected from (cyclopropyl)methyl and (cyclopropyl)ethyl; $(C_3$–$C_4)$alkenyl and alkynyl monosubstituted amino group substitution selected from allyl and propynyl; $(C_2$–$C_7)$azacycloalkyl and substituted $(C_2$–$C_7)$azacycloalkyl group substitution selected from 4-methylpiperidine, 4-hydroxypiperidine and 4-(hydroxymethyl)piperidine; substituted 1-azaoxacycloalkyl group substitution selected from 2-$(C_1$–$C_3)$alkylmorpholinyl; [1,n]-diazacycloalkyl and substituted [1,n]-diazacycloalkyl group selected from piperazinyl and 4-$(C_1$–$C_3)$alkylpiperazinyl; 1-azathiacycloalkyl and substituted 1-azathiacycloalkyl group selected from thiomorpholinyl and 2-$(C_1$–$C_3)$alkylthiomorpholinyl; (heterocycle)methylamino group selected from 2- or 3-thienylmethylamino and 2-, 3- or 4-pyridylmethylamino; 1,1-disubstituted hydrazino group selected from 1,1-dimethylhydrazino and N-aminopiperidinyl. [β or γ-$(C_1$–$C_3)$acylamido]alkylamino group substitution selected from 2-(acetamido)ethyl; β or γ-$(C_1$–$C_3)$alkoxyalkylamino group substitution selected from 2-methoxyethyl, 2-ethoxyethyl, 2,2-diethoxyethyl, 2-methoxypropyl and 3-methoxypropyl; β, γ or δ $(C_2$–$C_4)$hydroxyalkylamino selected from 4-hydroxybutyl and 3-hydroxypropyl;

or R$^3$ and W taken together are selected from —$(CH_2)_n$N—, n=3, and R$^5$ is selected from hydrogen and trifluoroacetyl;

R$^6$ is selected from hydrogen; straight or branched $(C_1$–$C_3)$alkyl group selected from methyl, ethyl, n-propyl or 1-methylethyl;

R$^7$ is selected from hydrogen; straight or branched $(C_1$–$C_3)$alkyl group selected from methyl, ethyl, n-propyl or 1-methylethyl; with the proviso that R$^6$ and R$^7$ cannot both be hydrogen;

or R$^6$ and R$^7$ taken together are —$(CH_2)_2$ B $(CH_2)_2$—, wherein B is selected from $(CH_2)_n$ and n=0–1, —NH, —N($C_1$–$C_3$)alkyl [straight or branched], —N($C_1$–$C_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Also included in the present invention are compounds useful as intermediates for producing the above compounds of formula I and II. Such intermediates include those having the formula III:

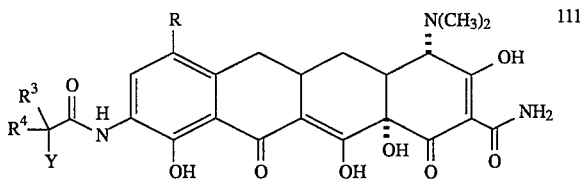

wherein:

Y is selected from $(CH_2)_nX$, n=0–5, X is halogen selected from bromine, chlorine, fluorine or iodine;

R is a halogen selected from bromine, chlorine, fluorine and iodine; or R=—$NR^1R^2$ and when R=—$NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl;

and when $R^1$=methyl or ethyl, $R^2$=methyl, ethyl, n-propyl, 1-methylethyl, n-butyl, 1-methylpropyl or 2-methylpropyl;

and when $R^1$=n-propyl, $R^2$=n-propyl, 1-methylethyl, n-butyl, 1-methylpropyl or 2-methylpropyl;

and when $R^1$=1-methylethyl, $R^2$=n-butyl, 1-methylpropyl or 2-methylpropyl;

and when $R^1$=n-butyl, $R^2$=n-butyl, 1-methylpropyl or 2-methylpropyl;

and when $R^1$=1-methylpropyl, $R^2$=2-methylpropyl;

$R^3$ is selected from hydrogen; straight or branched ($C_4$–$C_8$)alkyl group selected from butyl, isobutyl, pentyl, hexyl, heptyl and octyl;

α-mercapto($C_1$–$C_4$)alkyl group selected from mercaptomethyl, α-mercaptoethyl, α-mercapto-1-methylethyl and α-mercaptopropyl;

α-hydroxy-($C_1$–$C_4$)alkyl group selected from hydroxymethyl, α-hydroxyethyl, α-hydroxy-1-methylethyl and α-hydroxypropyl; carboxyl($C_1$–$C_8$)alkyl group;

($C_6$–$C_{10}$)aryl group selected from phenyl, α-naphthyl and β-naphthyl; substituted ($C_6$–$C_{10}$)aryl group (substitution selected from hydroxy, halogen, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy);

($C_7$–$C_9$)aralkyl group selected from benzyl, 1-phenylethyl, 2-phenylethyl and phenylpropyl;

substituted ($C_7$–$C_9$)aralkyl group [substitution selected from halo, ($C_1$–$C_4$)alkyl, nitro, hydroxy, amino, mono- or di-substituted ($C_1$–$C_4$)alkylamino, ($C_1$–$C_4$)alkoxy, ($C_1$–$C_4$)alkylsulfonyl, cyano and carboxy];

$R^4$ is selected from hydrogen and ($C_1$–$C_6$)alkyl selected from methyl, ethyl, propyl, isopropyl, butyl, isobutyl, pentyl and hexyl;

when $R^3$ does not equal $R^4$ the stereochemistry of the asymmetric carbon (i.e. the carbon bearing the substituent W) maybe be either the racemate (DL) or the individual enantiomers (L or D); and the pharmacologically acceptable organic and inorganic salts or metal complexes;

Preferred compounds are compounds according to the above formula III wherein:

Y is selected from $(CH_2)_nX$, n=0–5, X is halogen selected from bromine., chlorine, fluorine or iodine;

R is a halogen selected from bromine, chlorine, fluorine and iodine; or R=—$NR^1R^2$ and when R=—$NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl;

and when $R^1$=methyl or ethyl, $R^2$=methyl, ethyl, n-propyl, 1-methylethyl, n-butyl, 1-methylpropyl or 2-methylpropyl;

$R^3$ is selected from hydrogen; straight or branched ($C_4$–$C_8$)alkyl group selected from butyl, isobutyl, pentyl, hexyl, heptyl and octyl;

α-hydroxy($C_1$–$C_4$)alkyl group selected from hydroxymethyl, α-hydroxyethyl, α-hydroxy-1-methylethyl and α-hydroxypropyl;

carboxyl($C_1$–$C_8$)alkyl group; ($C_6$–$C_{10}$)aryl group selected from phenyl, α-naphthyl and β-naphthyl;

substituted($C_6$–$C_{10}$)aryl group (substitution selected from hydroxy, halogen, ($C_1$–$C_4$)alkoxy, ($C_1$–$C_4$)alkoxycarbonyl and carboxy); ($C_7$–$C_9$)aralkyl group selected from benzyl, 1-phenylethyl, 2-phenylethyl and phenylpropyl; substituted ($C_7$–$C_9$)aralkyl group [substitution selected from halo, ($C_1$–$C_4$)alkyl, ($C_1$–$C_4$)alkoxy, ($C_1$–$C_4$)alkylsulfonyl, cyano and carboxy];

$R^4$ is selected from hydrogen and ($C_1$–$C_4$)alkyl selected from methyl, ethyl, propyl, isopropyl, butyl and isobutyl;

when $R^3$ does not equal $R^4$ the stereochemistry of the asymmetric carbon (i.e. the carbon bearing the substituent W) maybe be either the racemate (DL) or the individual enantiomers (L or D); and the pharmacologically acceptable organic and inorganic salts or metal complexes.

Particularly preferred compounds are compounds according to formula III wherein:

Y is selected from $(CH_2)_nX$, n=0–5, X is halogen selected from bromine, chlorine, fluorine or iodine;

R is a halogen selected from bromine, chlorine, fluorine and iodine; or R=—$NR^1R^2$ and when R=—$NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl;

and when $R^1$=methyl or ethyl, $R^2$=methyl, ethyl, n-propyl, 1-methylethyl, n-butyl, 1-methylpropyl or 2-methylpropyl;

$R^3$ is selected from hydrogen; straight or branched ($C_4$–$C_6$)alkyl group selected from butyl, isobutyl, pentyl and hexyl; ($C_6$–$C_{10}$)aryl group selected from 5 phenyl, α-naphthyl and β-naphthyl; ($C_7$–$C_9$)aralkyl group selected from benzyl, 1-phenylethyl, 2-phenylethyl and phenylpropyl;

$R^4$ is selected from hydrogen and ($C_1$–$C_3$)alkyl selected from methyl, ethyl, propyl and isopropyl;

when $R^3$ does not equal $R^4$ the stereochemistry of the asymmetric carbon (i.e. the carbon bearing the substituent W) maybe be either the racemate (DL) or the individual enantiomers (L or D); and the pharmacologically acceptable organic and inorganic salts or metal complexes.

Compounds of special interest are compound according to formula III wherein:

Y is selected from $(CH_2)_nX$, n=0–5, X is halogen selected from bromine, chlorine, fluorine or iodine;

R is a halogen selected from bromine, chlorine and iodine; or R=—$NR^1R^2$ and when R=—$NR^1R^2$ and $R^1$=methyl or ethyl, $R^2$=methyl or ethyl, $R^3$ is selected from hydrogen;

$R^4$ is selected from hydrogen and $(C_1-C_2)$alkyl selected from methyl and ethyl;

when $R^3$ does not equal $R^4$ the stereochemistry of the asymmetric carbon (i.e. the carbon bearing the substituent W) maybe be either the racemate (DL) or the individual enantiomers (L or D); and the pharmacologically acceptable organic and inorganic salts or metal complexes.

DESCRIPTION OF THE PREFERRED EMBODIMENTS

The novel compounds of the present invention may be readily prepared in accordance with the following schemes.

The preferred method for producing 7-(substituted)-9-[(substituted glycyl)amido]-6-demethyl-6-deoxytetracyclines or the mineral acid salts, 3, is shown in scheme I. This method uses common intermediates which are easily prepared by reacting commercially available haloacyl halides of the formula:

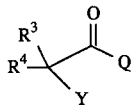

wherein Y, $R^3$ and $R^4$ are as defined hereinabove and Q is halogen selected from bromine, chlorine, iodine and fluorine; with 9-amino-7-(substituted)-6-demethyl-6-deoxytetracycline or its mineral acid salt, 1, to give straight or branched 9-[(haloacyl)amido]-7-(substituted)-6-demethyl-6-deoxytetracyclines or mineral acid salts, 2, in almost quantitative yield. The above intermediates, straight or branched 9-[(haloacyl)amido]-7-(substituted)-6-demethyl-6-deoxytetracyclines or mineral acid salts, 2, react with a wide variety of nucleophiles, especially amines, having the formula WH, wherein W is as defined hereinabove, to give a new 7-(substituted)-9-[(substituted glycyl)amido]-7-(substituted)-6-demethyl-6-deoxytetracyclines or the mineral acid salts, 3 of the present invention.

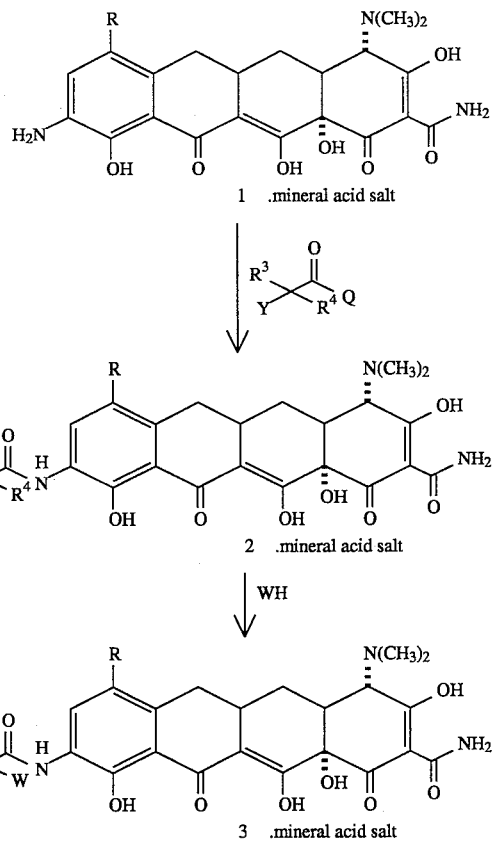

In accordance with scheme I, 9-amino-7-(substituted)-6-demethyl-6-deoxytetracycline or its mineral acid salt, 1, is mixed with a) a polar-aprotic solvent such as 1,3-dimethyl-3,4,5,6-tetrahydro-2(1H)pyrimidone, herein after called DMPU, hexamethylphosphoramide herein after called HMPA, dimethylformamide, dimethylacetamide, N-methylpyrrolidone, 1,2-dimethoxyethane or equivalent thereof;

b) an inert solvent such as acetonitrile, methylene chloride, tetrahydrofuran, chloroform, carbon tetrachloride, 1,2-dichloroethane, tetrachloroethane, diethyl ether, t-butyl methyl ether, isopropyl ether or equivalent thereof;

c) a base such as sodium carbonate, sodium bicarbonate, sodium acetate, potassium carbonate, potassium-bicarbonate, triethylamine, cesium carbonate, lithium carbonate or bicarbonate equivalents; and d) a straight or branched haloacyl halide of the formula:

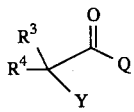

wherein Y, $R^3$, $R^4$ and Q are as hereinabove defined, such as bromoacetyl bromide, chloroacetyl chloride, 2-bromopropionyl bromide or equivalent thereof; the halo, Y, and halide, Q, in the haloacyl halide can be the same or different halogen and is selected from bromine, chlorine, iodine and fluorine; Y is $(CH_2)_nX$, $n=0-5$, X is halogen;

e) for 0.5 to 5 hours at from room temperature to the reflux temperature of the reaction; to form the corresponding 9-[(haloacyl)amido-7-(substituted)-6-demethyl-6-deoxytetracycline, 2, or its mineral acid salt.

The intermediate, 9-[(haloacyl) amido]-7-(substituted)-6-demethyl-6-deoxytetracycline or its mineral acid salt, 2, is treated, under an inert atmosphere of helium, argon or nitrogen, with a) a nucleophile WH such as an amine, substituted amine or equivalent thereof for example methylamine, dimethylamine, ethylamine, n-butylamine, propylamine or n,hexylamine;

b) a polar-aprotic solvent such as DMPU, HMPA dimethylformamide, dimethylacetamide, N-methylpyrrolidone or 1,2-dimethoxyethane;

c) for from 0.5–2 hours at room temperature or under reflux temperature to produce the desired 7-(substituted)-9-[(substituted glycyl)amido]-6-demethyl-6-deoxytetracycline, 3, or its mineral acid salt.

Scheme II

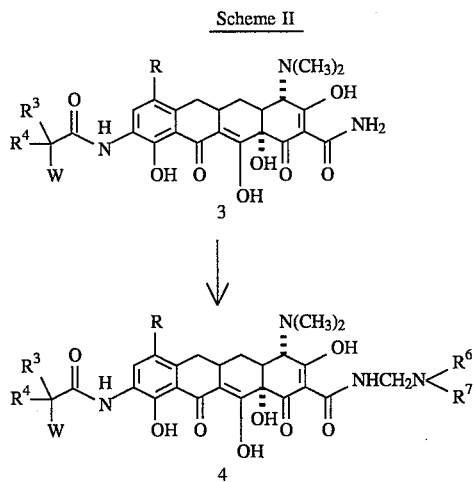

In accordance with Scheme II, compounds of formula 3 are N-alkylated in the presence of formaldehyde and either a primary amine such as methylamine, ethylamine, benzylamine, methyl glycinate, (L or D)alanine, (L or D)lysine of their substituted congeners; or a secondary amine such as morpholine, pyrrolidine, piperidine or their substituted congeners to give the corresponding Mannich base adduct, 4.

The 7-(substituted)-9-[(substituted glycyl)amido]-6-demethyl-6-deoxytetracyclines may be obtained as metal complexes such as aluminum, calcium, iron, magnesium, manganese and complex salts; inorganic and organic salts and corresponding Mannich base adducts using methods known to those skilled in the art (Richard C. Larock, Comprehensive Organic Transformations, VCH Publishers, 411–415, 1989). It is well known to one skilled in the art that an appropriate salt form is chosen based on physical land chemical stability, flowability, hygroscopicity and solubility. Preferably, the 7-(substituted)-9-[(substituted glycyl)amido]-6-demethyl-6-deoxytetracyclines are obtained as inorganic salt such as hydrochloric, hydrobromic, hydroiodic, phosphoric, nitric or sulfate; or organic salt such as acetate, benzoate, citrate, cysteine or other amino acids, fumarate, glycolate, maleate, succinate, tartrate, alkylsulfonate or arylsulfonate. Depending on the stoichiometry of the acids used, the salt formation occurs with the C(4)-dimethylamino group (1 equivalent of acid) or with both the C(4)-dimethylamino group and the W group (2 equivalents of acid). The salts are preferred for oral and parenteral administration.

Some of the compounds of the hereinbefore described Schemes have centers of asymmetry at the carbon bearing the W substituent. The compounds may, therefore, exist in at least two (2) stereoisomeric forms. The present invention encompasses the racemic mixture of stereoisomers as well as all stereoisomers of the compounds whether free from other stereoisomers or admixed with stereoisomers in any proportion of enantiomers. The absolute configuration of any compound may be determined by conventional X-ray crystallography.

The stereochemistry centers on the tetracycline unit (i.e. C-4, C-4a, C-5a and C-12a) remain intact throughout the reaction sequences.

BIOLOGICAL ACTIVITY

Methods for in Vitro antibacterial evaluation (Table I)

The minimum inhibitory concentration (MIC), the lowest concentration of the antibiotic which inhibits growth of the test organism, is determined by the agar dilution method using 0.1 ml Muller-Hinton II agar (Baltimore Biological Laboratories) per well. An inoculum density of $1-5\times10^5$ CFU/ml, and an antibiotic concentrations range of 32–0.004 microgram/ml is used. MIC is determined after the plates are incubated for 18 hours at 35° C. in a forced air incubator. The test organisms comprise strains that are sensitive to tetracycline and genetically defined strains that are resistant to tetracycline, due to inability to bind bacterial ribosomes (tetM).

E. coli in Vitro Protein Translation System (Table II)

An in vitro, cell free, protein translation system using extracts from E. coli strain MRE600 (tetracycline sensitive) and a derivative of MRE600 containing the tetM determinant has been developed based on literature methods [J. M. Pratt, Coupled Transcription-translation in Prokaryotic Cell-free Systems, Transcription and Translation, a Practical Approach, (B. D. Hames and S. J. Higgins, eds) p. 179–209, IRL Press, Oxford-Washington, 1984].

Using the system described above, the tetracycline compounds of the present invention are tested for their ability to inhibit protein synthesis in vitro. Briefly, each 10 microliter reaction contains S30 extract (a whole extract) made from either tetracycline sensitive cells or an isogenic tetracycline resistant (tetM) strain, low molecular weight components necessary for transcription and translation (i.e. ATP and GTP), a mix of 19 amino acids (no methionine), $^{35}S$ labeled methionine, DNA template (either pBR322 or pUC119), and either DMSO (control) or the novel tetracycline compound to be tested ("novel TC") dissolved in DMSO.

The reactions are incubated for 30 minutes at 37 C. Timing is initiated with the addition of the S30 extract, the last component to be added. After 30 minutes, 2.5 µl of the reaction is removed and mixed with 0.5 ml of 1N NaOH to destroy RNA and tRNA. Two ml of 25% trichloroacetic acid is added and the mixture incubated at room temperature for 15 minutes. The trichloroacetic acid precipitated material is collected on Whatman GF/C filters and washed with a solution of 10% trichloroacetic acid. The filters are dried and the retained radioactivity, representing incorporation of $^{35}S$-methionine into polypeptides, is counted using standard liquid scintillation methods.

The percent inhibition (P.I.) of protein synthesis is determined to be:

$$P.I. = 100 - \left( \frac{\text{Retained radioactivity of novel TC containing sample}}{\text{Retained radioactivity of the DMSO control reaction}} \right) \times 100$$

In Vivo Antibacterial Evaluation

The therapeutic effects of tetracyclines are determined against an acute lethal infection with *Staphylococcus aureus* strain Smith (tetracycline sensitive). Female, mice, strain CD-1 (Charles River Laboratories), 20±2 grams, are challenged by an intraperitoneal injection of sufficient bacteria (suspended in hog mucin) to kill non-treated controls within 24–48 hours. Antibacterial agents, contained in 0.5 ml of 0.2% aqueous agar, are administered subcutaneously or orally 30 minutes after infection. When an oral dosing schedule is used, animals are deprived of food for 5 hours before and 2 hours after infection. Five mice are treated at each dose level. The 7 day survival ratios from 3. separate tests are pooled for calculation of median effective dose ($ED_{50}$).

Testing Results

The claimed compounds exhibit antibacterial activity against a spectrum of tetracycline sensitive and resistant Gram-positive and Gram-negative bacteria, especially, strains of *E. coli, S. aureus* and *E. faecalis*, containing tetM and tetD resistance determinants; and *E. coli* containing the tetB and tetD resistance determinants. Notable are compounds D, G, and K, as shown in Table I, which demonstrated excellent in vitro activity against tetracycline resistant strains containing the tetM resistance determinant (such as *S. aureus* UBMS 88-5, *S. aureus* UBMDS 90-1 and 90-2, *E. coli* UBMS 89-1 and 90-4) and tetracycline resistant strains containing tetB resistance determinants (such as *E. coli* UBMS 88-1 and *E. coli* TN10C tetB). These compounds also have good activity against *E. coli* tetA, *E. Coli* tetC and *E. coli* tetD and are equally as effective as minocycline against susceptible strains and are superior to that of minocycline against a number of recently isolated bacteria from clinical sources (Table I).

Minocycline and compounds B, C, D, G and H are assayed in vitro for their ability to inhibit protein synthesis taking place on either wild type or tetM protected ribosomes using a coupled transcription and translation system. All compounds are found to effectively inhibit protein synthesis occurring on wild type ribosomes, having equivalent levels of activity. Minocycline is unable to inhibit protein synthesis occurring on tetM protected ribosomes. In contrast, compounds B, C, D, G and H are effective at inhibiting protein synthesis occurring on tetM protected ribosomes (Table II).

Compounds B, C, D, G and H bind reversibly to its target (the ribosome) since bacterial growth resumes when the compound is removed from the cultures by washing of the organism. Therefore, the ability of these compounds to inhibit bacterial growth appears to be a direct consequence of its ability to inhibit protein synthesis at the ribosome level.

The activity of compound G against tetracycline susceptible organisms is also demonstrated in vivo in animals infected with *S. aureus* Smith with $ED_{50}$'s between 1–2 mg/kg when administered intravenously, and $ED_{50}$'s of 4–8 mg/kg when given orally.

The improved efficacy of compounds D, G and K is demonstrated by the in vitro activity against isogenic strains into which the resistance determinants, such as tetM and tetB, were cloned (Table I); and the inhibition of protein synthesis by tetM ribosomes (Table II).

As can be seen from Table I and II, compounds of the invention may also be used to prevent or control important veterinary diseases such as diarrhea, urinary tract infections, infections of skin and skin structure, ear, nose and throat infections, wound infections, mastitis and the like.

| | COMPOUND LEGEND FOR TABLES |
|---|---|
| A | [7S-(7alpha,10aalpha)]-N-[9-(Aminocarbonyl)-4,7-bis(dimethylamino)-5,5a,5,5a,7,10,10a,12-octahydro-1,8,10a,11-tetrahydroxy-10,12-dioxo-2-naphthacenyl]-1-(trifluoroacetyl)-2-pyrrolidinecarboxamide dihydrochloride |
| B | [4S-(4alpha,12aalpha)]-4,7-Bis(dimethylamino)-1,4,4a,5,5a,6,11,12a-octahydro-3,10,12,12a-tetrahydroxy-9-[[[(2-(methoxyethyl)-amino]acetyl]amino]-1,11-dioxo-2-naphthacene-carboxamide dihydrochloride |
| C | [4S-(4alpha,12aalpha)]-9-[[[(2,2-Diethoxy-ethyl)amino]acetyl]amino]-4,7-bis(dimethylamino)-1,4,4a,5,5a,6,11,12a-octahydro-3,10,12,12a-tetrahydroxy-1,11-dioxo-2-naphthacene-carboxamide dihydrochloride |
| D | [4S-(4alpha,12aalpha)]-4,7-Bis(dimethylamino)-1,4,4a,5,5a,6,11,12a-octahydro-3,10,12,12a-tetrahydroxy-1,11-dioxo-9-[[[(2-propenylamino)acetyl]amino]-2-naphthacenecarboxamide dihydrochloride |
| E | [4S-(4alpha,12aalpha)]-4,7-bis(dimethylamino)-1,4,4a,5,5a,6,11,12a-octahydro-3,10,12,12a-tetrahydroxy-1,11-dioxo-9-[[[(2-pyridinylmethyl)amino]acetyl]amino-2-naphthacenecarboxamide dihydrochloride |
| F | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-4-thiomorpholineacetamide dihydrochloride |
| G | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-4-methyl-1-piperidine-acetamide dihydrochloride |
| H | [4S-(4alpha,12aalpha)]-4,7-Bis(dimethylamino)-1,4,4a,5,5a,6,11,12a-octahydro-3,10,12,12a-tetrahydroxy-9-[[[(3-methoxypropyl)-amino]acetyl]amino]-1,11-dioxo-2-naphthacene-carboxamide dihydrochloride |
| I | 7[7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-4-methyl-1-piperazine-acetamide dihydrochloride |
| J | [4S-(4alpha,12aalpha)]-4,7-Bis(dimethylamino)-9-[[(heptylamino)acetyl]amino]-1,4,4a,5,5a,6,11,12a-octahydro-3,10,12,12a-tetrahydroxy-1,11-dioxo-2-naphthacenecarboxamide dihydrochloride |
| K | [4S-(4alpha,12aalpha)]--9-[[(Cyclopropyl-methyl)amino]acetyl]amino]-4,7-bis(dimethylamino)-1,4,4a,5,5a,6,11,12a-octahydro-3,10,12,12a-tetrahydroxy-1,11-dioxo-2-naphthacene-carboxamide dihydrochloride |
| L | [4S-(4alpha,12aalpha)]-4,7-Bis(dimethylamino)-1,4,4a,5,5a,6,11,12a-octahydro-3,10,12,12a-tetrahydroxy-1,11-dioxo-9-[[[(undecyl-amino)acetyl]amino]-2-naphthacenecarboxamide dihydrochloride |
| M | [4S-(4alpha,12aalpha)]-9-[(Bromoacetyl)-amino]-4,7-bis(dimethylamino)-1,4,4a,5,5a,6,11,12a-octahydro-3,10,12,12a-tetrahydroxy-1,11-dioxo-2-naphthacenecarboxamide dihydrochloride |
| N | Tetracycline |
| O | Minocycline |
| P | [4S-(4alpha,12aalpha)]-4,7-Bis(dimethylamino)-1,4,4a,5,5a,6,11,12a-octahydro-3,10,-12,12a-tetrahydroxy-9-[[[(2-hydroxyethyl)-amino]acetyl]amino]-1,11-dioxo-2-naphthacene- |

COMPOUND LEGEND FOR TABLES

Q [4S-(4alpha,12alpha)]-4,7-Bis(dimethyl-amino)-1,4,4a,5,5a,6,11,12a-octahydro-3,10,-12,12a-tetrahydroxy-9-[[[(2-hydroxyethyl)-methylamino]acetyl]amino-1,11-dioxo-2-naphthacenecarboxamide R [4S-(4alpha,12aalpha)]-4,7-Bis(dimethyl-4-amino-1-amino-1,4,4a,5,5a,6,11,12a-octa-hydro-3,10,12,12a-tetrahydroxy-9-[[[(4-(hydroxybutyl)amino]acetyl]amino]-1,11-dioxo-2-naphthacenecarboxamide S [4S-(4alpha,12aalpha)]-4,7-Bis(dimethyl-amino)-1,4,4a,5,5a,6,11,12a-octahydro-3,10,-12,12a-tetrahydroxy-1,11-dioxo-9-[[[2,2,2-trifluoroethyl)amino]acetyl]amino-2-naphtha-cenecarboxamide T [4S-(4alpha,12aalpha)]-4,7-Bis(dimethyl-amino)-9-[[[(2-fluoroethyl)amino]acetyl]-amino]-1,4,4a,5,5a,6,11,12a-octahydro-3,10,12,12a-tetrahydroxy-1,11-dioxo-2-naphthacenecarboxamide U [4S-(4alpha,12aalpha)]-4,7-Bis(dimethyl-amino)-1,4,4a,5,5a,6,11,12a-octahydro-3,10,12,12a-tetrahydroxy-1,11-dioxo-9-[[[[2-(1-piperidinyl)ethyl]amino]acetyl]-amino]-2-naphthacenecarboxamide V [4S-(4alpha,12aalpha)]-4,7-Bis(dimethyl-amino)-1,4,4a,5,5a,6,11,12a-octahydro-3,10,-12,12a-tetrahydroxy-9-[[[methyl-2-propynyl-amino]acetyl]amino]-1,11-dioxo-2-naphtha-cenecarboxamide W [4S-(4alpha,12aalpha)]-4,7-Bis(dimethyl-amino)-1,4,4a,5,5a,6,11,12a-octahydro-3,10,-12,12a-tetrahydroxy-hydroxy-1,11-dioxo-9-[[[(1-piperidinylamino)acetyl]amino]-2-naphthacenecarboxamide X [4S-(4-alpha,12aalpha)]-4,7-Bis(dimethyl-amino)-1,4,4a,5,5a,6,11,12a-octahydro-3,10,-12,12a-tetrahydroxy-1,11-dioxo-9-[[[(phenyl-methoxy)amino]acetyl]amino]-2-naphthacene-carboxamide

TABLE I

ANTIBACTERIAL ACTIVITY OF 9-[(SUBSTITUTED GLYCYL)AMIDO]-6-DEMETHYL-6-DEOXYTETRACYCLINES
MIC (μg/ml)

| Organism | A | B | C | D | E | F | G | H | I | J | K | L | M | N | O |
|---|---|---|---|---|---|---|---|---|---|---|---|---|---|---|---|
| E. coli UBMS 88-1 Tet B | 8 | 2 | 16 | 1 | 16 | >32 | 2 | 2 | 8 | 2 | 0.5 | 32 | >32 | >32 | 16 |
| E. coli J3272 Tet sens. | 8 | 2 | 8 | 0.5 | NT | >32 | 1 | 1 | NT | NT | NT | NT | 16 | 0.5 | 0.5 |
| E. coli MC 4100 Tet sens. | NT | NT | NT | NT | 2 | NT | NT | NT | 1 | 1 | 0.12 | 2 | NT | NT | NT |
| E. coli PRP1 Tet A | >32 | 8 | >32 | 8 | 32 | >32 | 2 | 4 | 16 | 2 | 4 | 32 | >32 | 32 | 4 |
| E. coli MC 4100 TNIOC Tet B | 8 | 2 | 8 | 1 | NT | >32 | 2 | 2 | NT | NT | NT | NT | >32 | >32 | 8 |
| E. coli J3272 Tet C | 8 | 4 | 16 | 1 | 16 | >32 | 1 | 1 | 8 | 2 | 0.5 | 32 | >32 | >32 | 2 |
| E. coli UBMS 89-1 Tet M | 8 | 2 | 4 | 0.5 | 8 | >32 | 0.5 | 2 | 8 | 0.5 | 0.5 | 16 | 4 | 8 | 8 |
| E. coli UBMS 89-2 Tet sens. | 8 | 2 | 8 | 0.5 | 16 | >32 | 2 | 1 | 8 | 2 | 0.5 | 16 | 32 | 1 | 0.5 |
| E. coli J2175 | 8 | 2 | 8 | 0.5 | 16 | >32 | 1 | 1 | 8 | 2 | 0.5 | 16 | 32 | 1 | 0.5 |
| E. coli BAJ9003 IMP MUT | 1 | 0.25 | 0.5 | 0.12 | 1 | 0.5 | 0.12 | 0.12 | 0.5 | 0.25 | 0.12 | 1 | 0.25 | 0.25 | 0.03 |
| E. coli UBMS 90-4 Tet M | NT | 2 | 4 | 0.5 | 8 | >32 | 1 | 1 | 8 | 2 | 0.5 | 32 | NT | 16 | >32 |
| E. coli UBMS 90-5 | 4 | 2 | 8 | 0.5 | 16 | >32 | 2 | 2 | 8 | 2 | 0.5 | 16 | 16 | 1 | 0.5 |
| E. coli #311 (MP) | 8 | 2 | 8 | 0.5 | 8 | >32 | 1 | 1 | 8 | 2 | 0.5 | 8 | 8 | 1 | 0.25 |
| E. coli ATCC 25922 | 8 | 2 | 8 | 0.5 | 8 | 32 | 1 | 1 | 8 | 2 | 0.5 | 8 | 16 | 0.5 | 0.5 |
| E. coli J3272 Tet D | 2 | 1 | 4 | 0.25 | 8 | 16 | 0.25 | 0.5 | 4 | 2 | 0.25 | 32 | 32 | >32 | 8 |
| S. mariescens FPOR 8733 | >32 | >32 | >32 | 8 | >32 | >32 | 16 | 16 | >32 | 16 | 8 | >32 | >32 | 32 | 2 |
| X. maltophilia NEMC 87210 | | | | | | | | | | | | | | | |
| Ps. acrygubisa ATCC 27853 | >32 | >32 | >32 | 16 | >32 | >32 | 32 | 32 | >32 | >32 | 16 | >32 | >32 | 8 | 8 |
| S. aureus NEMC 8769 | 1 | 0.5 | 0.25 | 0.12 | 8 | 0.25 | 0.12 | 0.25 | 0.5 | no growth | 1 | 0.5 | 0.12 | 0.03 | <0.015 |
| S. aureus UBMS 88-4 | 4 | 0.5 | 1 | 0.25 | 8 | 1 | 0.5 | 1 | 2 | 0.5 | 0.5 | 0.5 | 0.5 | 0.06 | 0.03 |
| S. aureus UBMS 88-5 Tet M | 4 | 1 | 1 | 0.25 | 8 | 1 | 0.5 | 0.5 | 4 | 0.5 | 1 | 16 | 1 | >32 | 4 |
| S. aureus UBMS 88-7 Tet K | 16 | 16 | 8 | 8 | 32 | 4 | 0.5 | 8 | 16 | 1 | 4 | 2 | 2 | >32 | 0.12 |
| S. aureus UBMS 90-1 Tet M | 8 | 2 | 1 | 0.5 | 8 | 1 | 0.5 | 2 | 8 | 1 | 1 | 16 | 1 | 32 | 4 |
| S. aureus UBMS 90-3 | 1 | 0.5 | 0.5 | 0.25 | 4 | 1 | 0.5 | 0.5 | 2 | 0.5 | 0.5 | 0.5 | 0.5 | 0.06 | 0.03 |
| S. aureus UBMS 90-2 Tet M | 2 | 0.5 | 1 | 0.25 | 8 | 1 | 0.5 | 0.5 | 2 | 0.5 | 0.5 | 4 | 0.5 | 32 | 2 |
| S. aureus IVES 2943 | 16 | 32 | 8 | 8 | >32 | 4 | 0.5 | 16 | >32 | 0.5 | 8 | 16 | 4 | >32 | 2 |
| S. aureus ROSE (MP) | 32 | 32 | 16 | 8 | >32 | 8 | 1 | 16 | >32 | 2 | 8 | 16 | 8 | >32 | 0.5 |
| S. aureus ATCC 29213 | 4 | 1 | 1 | 0.25 | 8 | 1 | 0.5 | 1 | 2 | 0.5 | 1 | 1 | 0.5 | 0.06 | 0.03 |
| S. hemolyticus AVHAH 88-3 | 8 | 2 | 2 | 0.5 | 16 | 4 | 1 | 2 | 16 | 2 | 2 | 8 | 2 | 0.5 | 0.12 |
| Enterococcus 12201 | 0.5 | 0.5 | 1 | 0.25 | 4 | 1 | 0.25 | 0.5 | 2 | 0.5 | 0.25 | 4 | 1 | 32 | 8 |
| E. faecalis ATCC 29212 | 2 | 0.25 | 0.5 | 0.12 | 2 | 0.25 | 0.12 | 0.25 | 1 | 0.25 | 0.25 | 2 | 0.5 | 8 | 1 |

| Organism | P | Q | R | S | T | U | V | W | X |
|---|---|---|---|---|---|---|---|---|---|
| E. coli UBMS 88-1 Tet B | >32 | 32 | >32 | 32 | 16 | >32 | >32 | >32 | >32 |
| E. coli J3272 Tet sens. | NT | NT | NT | NT | NT | NT | NT | NT | NT |
| E. coli MC 4100 Tet sens. | 4 | 4 | 8 | 16 | 2 | 4 | 32 | 32 | 4 |
| E. coli PRP1 Tet A | >32 | >32 | >32 | >32 | >32 | >32 | >32 | >32 | >32 |
| E. coli MC 4100 TNIOC Tet B | >32 | >32 | >32 | >32 | 16 | 32 | >32 | >32 | >32 |
| E. coli J3272 Tet C | >32 | >32 | >32 | >32 | >32 | 16 | >32 | >32 | >32 |
| E. coli UBMS 89-1 Tet M | >32 | 32 | 32 | 32 | 8 | 16 | >32 | >32 | 16 |

TABLE I-continued

ANTIBACTERIAL ACTIVITY OF 9-[(SUBSTITUTED GLYCYL)AMIDO]-6-DEMETHYL-6-DEOXYTETRACYCLINES
MIC (μg/ml)

| | | | | | | | | | |
|---|---|---|---|---|---|---|---|---|---|
| E. coli UBMS 89-2 Tet sens. | >32 | 32 | 32 | >32 | 16 | 32 | >32 | >32 | >32 |
| E. coli J2175 | 32 | 32 | 32 | >32 | 16 | 32 | >32 | >32 | >32 |
| E. coli BAJ9003 IMP MUT | 2 | 2 | 4 | 1 | 1 | 2 | 4 | 16 | 1 |
| E. coli UBMS 90-4 Tet M | 32 | 16 | 32 | >32 | 8 | 16 | >32 | >32 | >32 |
| E. coli UBMS 90-5 | 32 | 32 | 32 | >32 | 16 | 16 | >32 | >32 | >32 |
| E. coli #311 (MP) | 16 | 32 | 32 | >32 | 16 | 16 | >32 | >32 | 16 |
| E. coli ATCC 25922 | 16 | 32 | 32 | >32 | 8 | 16 | >32 | >32 | 16 |
| E. coli J3272 Tet D | 16 | 32 | 8 | >32 | 8 | 8 | >32 | >32 | 16 |
| S. mariescens FPOR 8733 | >32 | 16 | 8 | >32 | >32 | >32 | >32 | >32 | >32 |
| X. maltophilia NEMC 87210 | >32 | 8 | 8 | 16 | 16 | 16 | 32 | >32 | 16 |
| Ps. acruginosa ATCC 27853 | >32 | >32 | >32 | >32 | >32 | >32 | >32 | >32 | >32 |
| S. aureus NEMC 8769 | 4 | 8 | 8 | 4 | 4 | 8 | 4 | >32 | 1 |
| S. aureus UBMS 88-4 | 8 | 8 | 8 | 4 | 4 | 8 | 4 | >32 | 1 |
| S. aureus UBMS 88-5 Tet M | 32 | 16 | 32 | 8 | 4 | 16 | 8 | >32 | 2 |
| S. aureus UBMS 88-7 Tet K | 32 | 32 | 32 | 32 | >32 | 16 | 32 | >32 | 4 |
| S. aureus UBMS 90-1 Tet M | 32 | 32 | 32 | 16 | 4 | 32 | 16 | >32 | 2 |
| S. aureus UBMS 90-3 | 8 | 8 | 8 | 4 | 2 | 8 | 4 | 16 | 1 |
| S. aureus UBMS 90-2 Tet M | 16 | 16 | 16 | 4 | 4 | 8 | 8 | >32 | 2 |
| S. aureus IVES 2943 | >32 | >32 | >32 | >32 | >32 | >32 | >32 | >32 | 8 |
| S. aureus ROSE (MP) | >32 | >32 | >32 | >32 | >32 | >32 | >32 | >32 | 16 |
| S. aureus SMITH (MP) | 4 | 8 | 8 | 1 | 1 | 8 | 4 | 16 | 0.5 |
| S. aureus IVES 1 983 | >32 | >32 | >32 | >32 | >32 | >32 | >32 | >32 | 8 |
| S. aureus ATCC 29213 | 8 | 16 | 16 | 4 | 4 | 8 | 4 | 32 | 1 |
| S. hemolyticus AVHAH 88-3 | 32 | 16 | 32 | 16 | 8 | 32 | 32 | >32 | 4 |
| Enterococcus 12201 | 8 | 4 | 8 | 4 | 2 | 8 | 8 | >32 | 4 |
| E. faecalis ATCC 29212 | 4 | 4 | 8 | 2 | 1 | 8 | 4 | >32 | 1 |

NT = Not tested

TABLE II

In Vitro Trancription and Translation
Sensitivity to Tetracycline Compounds

| | | % Inhibition | |
|---|---|---|---|
| Compound | Conc. | Wild Type S30 | TetM S30 |
| B | 1.0 mg/ml | 98 | 97 |
| | 0.25 mg/ml | 96 | 95 |
| | 0.06 mg/ml | 92 | 91 |
| C | 1.0 mg/ml | 98 | 96 |
| | 0.25 mg/ml | 95 | 84 |
| | 0.06 mg/ml | 88 | 65 |
| D | 1.0 mg/ml | 99 | 98 |
| | 0.25 mg/ml | 98 | 96 |
| | 0.06 mg/ml | 93 | 83 |
| G | 1.0 mg/ml | 99 | 99 |
| | 0.25 mg/ml | 97 | 92 |
| | 0.06 mg/ml | 90 | 83 |
| H | 1.0 mg/ml | 99 | 98 |
| | 0.25 mg/ml | 96 | 94 |
| | 0.06 mg/ml | 88 | 85 |
| O | 1.0 mg/ml | 98 | 68 |
| | 0.25 mg/ml | 89 | 43 |
| | 0.06 mg/ml | 78 | 0 |

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an tonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserve against the contaminating action of micoorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not be construed as limiting the scope of the invention.

EXAMPLE 1

[4S-(4alpha,12aalpha)]-9-[(Chloroacetyl)amino]-4,7-bis(dimethylamino)-1,4,4a,5,5a,6,11,12a-octahydro-3,10,12,12a-tetrahydroxy-1,11-dioxo-2-naphthacenecarboxamide dihydrochloride To a room temperature solution of 0.334 g of 9-amino-4,7-bis(dimethyamino)-6-demethyl-6-deoxytetracycline disulfate, 6 ml of 1,3-dimethyl-3,4,5,6-tetrahydro-2(1H)-pyrimidinone, hereinafter called DMPU, and 2 ml of acetonitrile is added 0.318 g of sodium carbonate. The mixture is stirred for 5 minutes followed by the addition of 0.068 g of chloroacetyl chloride. The reaction is stirred for 30 minutes, filtered, and the filtrate added dropwise to 100 ml of diethyl ether, containing 1 ml of 1M hydrochloric acid in diethyl ether. The resulting solid is collected and dried to give 0.340 g of the desired intermediate.

MS(FAB): m/z 549 (M+H).

EXAMPLE 2

[4S-(4alpha,12aalpha)]-9-[(Bromoacetyl)amino]-4,7-bis(dimethylamino)-1,4,4a,5,5a,6,11,12a-octahydro-3,10,12,12a-tetrahydroxy-1,11-dioxo-2-naphthacenecarboxamide monohydrobromide The title compound is prepared by the procedure of Example 1, using 6.68 g of 9-amino-4,7 -bis(dimethylamino)-6-demethyl-6-deoxytetracycline disulfate, 50 ml of DMPU, 30 ml of acetonitrile, 6.68 g of sodium carbonate and 0.215 g of bromoacetyl bromide. 5.72 g of the desired intermediate is obtained.

MS(FAB): m/z 593 (M+H).

EXAMPLE 3

[4S-(4alpha,12aalpha)]-9-[(2-Bromo-1-oxopropyl)amino]-4,7-bis(dimethylamino)-1,4,4a,5,5a,6,11,12a-octahydro-3,10,12,12a-tetrahydroxy-1,11-dioxo-2-naphthacenecarboxamide sulfate The title compound is prepared by the procedure of Example 1, using 1.00 g of 9-amino-4,7 -bis(dimethylamino)-6-demethyl-6-deoxytetracycline disulfate, 1.0 g of sodium carbonate and 0.648 g of 2-bromopropionyl bromide to give 0.981 g of the desired product.

MS(FAB): m/z 607 (M+H).

EXAMPLE 4

[4S-(4alpha,12aalpha)]-9-[(4-Bromo-1-oxobutyl)amino]-4,7-bis(dimethylamino)-1,4,4a,5,5a,6,11,12a-octahydro-3,10,12,12a-tetrahydroxy-1,11-dioxo-2-naphthacenecarboxamide dihydrochloride The title compound is prepared by the procedure of Example 1, using 1.34 g of 9-amino-4,7 -bis(dimethylamino)-6-demethyl-6-deoxytetracycline disulfate, 1.3 of sodium carbonate, 24 ml of DMPU, 8 ml of acetonitrile and 0.389 g of 4-bromobutyryl chloride to give 1.45 g of the desired product.

EXAMPLE 5

[7S-(7alpha,10aalpha)]-N-[9-(Aminocarbonyl)-4,7-bis(dimethylamino)-5,5a,6,7,10,10a,12-octahydro-1,8,10a,11-tetrahydroxy-10,12-dioxo-2-naphthacenyl]-1-trifluoroacetyl)-2-pyrrolidinecarboxamide dihydrochloride The title compound is prepared by the procedure of Example 1, using 0.334 g of 9-amino-4,7 -bis(dimethylamino)-6-demethyl-6-deoxytetracycline disulfate, 10 ml of DMPU, 2 ml of acetonitrile, 0.34 g of sodium carbonate and 7.5 ml of 0.1M (S)-(−)-N-(trifluoroacetyl)prolyl chloride to give 0.292 g of the desired product.

MS(FAB): m/z 666 (M+H).

EXAMPLE 6

4S-(4alpha,12aalpha)]-9-[[[(Cyclopropylmethyl)amino]acetyl]amino]-4,7-bis(dimethylamino)-1,4,4a,5,5a,6,11,12-a-octahydro-3,10,12,12a-tetrahydroxy-1,11-dioxo-2-naphthacenecarboxamide dihydrochloride A mixture Of 0.20 g of product from Example 2, 0.50 g of (aminomethyl)cyclopropane and 5 ml of DMPU, under Argon, is stirred at room temperature for 1 hour. The excess amine is removed in vacuo and the residue diluted with a small volume of methyl alcohol. The diluted reaction solution is added dropwise to a mixture of diethyl ether and 5 ml of 2-propanol. 1M Hydrochloric acid in diethyl ether is added until a solid is formed. The resulting solid is collected and dried to give 0.175 g of the desired product.

MS(FAB): m/z 584 (M+H) .

Substantially following the methods described in detail herein above in Example 6, the compounds of this invention listed below in Examples 7–16 are prepared.

| Example # | Name | Starting Material Prod. of Exp. | Reactant | Rx Time | MS(FAB): m/z |
|---|---|---|---|---|---|
| 7 | [4S-(4alpha,12aalpha)]-9-[[[(2,2-Diethoxyethyl)amino]acetyl]amino]-4,7-bis(dimethylamino)-1,4,4a,5,5a,6,11,-12a-octahydro-3,10,12,12a-tetrahydroxy-1,11-dioxo-2-naphthacenecarboxamide dihydrochloride | 2 or 1 | 2,2-Diethoxy-ethylamine | 3 hrs. | 646(M+H) |
| 8 | [4S-(4alpha,12aalpha)]-4,7-Bis(dimethyl-amino)-1,4,4a,5,5a,6,11,12a-octahydro-3,10,12,12a-tetrahydroxy-9-[[[2-(methoxy-ethyl)amino]acetyl]amino]-1,11-dioxo-2-naphthacenecarboxamide dihydrochloride | 2 or 1 | 2-Methoxy-ethylamine | 2 hr. | 588(M+H) |
| 9 | [4S-(4alpha,12aalpha)]-4,7-Bis(dimethyl-methylamino)-1,4,4a,5,5a,6,11,12a-octa-hydro-3,10,12,12a-tetrahydroxy-1,11-dioxo-9-[[(2-propenylamino)acetyl]amino]-2-naphthacenecarboxamide dihydrochloride | 2 or 1 | Allylamine | 2 hr. | 570(M+H) |
| 10 | [4S-(4alpha,12aalpha)]-4,7-Bis(dimethyl-amino)-1,4,4a,5,5a,6,11,12a-octahydro-3,10,12,12a-tetrahydroxy-9-[[[(3-methoxy-propyl)amino]acetyl]amino]-1,11-dioxo-2-naphthacenecarboxamide dihydrochloride | 2 or 1 | 3-Methoxy-propylamine | 2 hr. | 602(M+H) |
| 11 | [7S-(7alpha,10aalpha)]-N-[9-(Aminocar-bonyl)-4,7-bis(dimethylamino)-5,5a,6,6a,7,10,10a,12-octahydro-1,8,10a,11-tetra-hydroxy-10,12-dioxo-2-naphthacenyl]-4-thiomorpholineacetamide dihydrochloride | 2 | Thiomorpholine | 3 hr. | 616(M+H) |
| 12 | [7S-(7alpha,10aalpha)]-N-[9-(Amino-carbonyl)-4,7-bis(dimethylamino)-5,5a,-6,6a,7,10,10a,12-octahydro-1,8,10a,11-tetrahydroxy-10,12-dioxo-2-naphthacenyl]-4-methyl-1-piperidineacetamide dihydrochloride | 2 | 4-Methylpiperi-dine | 2 hrs. | 612(M+H) |
| 13 | [7S-(7alpha,10aalpha)]-N-[9-(Aminocar-bonyl)-4,7-bis(dimethylamino)-5,5a,6,-6a,7,10,10a,12-octahydro-1,8,10a,11-tetrahydroxy-10,12-dioxo-2-naphtha-cenyl]-4-methyl-1-piperazineacetamide dihydrochloride | 2 | 4-methyl-1-piperazine | 0.75 hr. | 613(M+H) |
| 14 | [4S-(4alpha,12aalpha)]-4,7-Bis(di-methylamino)-9-[[(heptylamino)acetyl]amino]-1,4,4a,5,5a,6,11,12a-octahydro-3,10,12;12a-tetrahydroxy-1,11-dioxo-2-naphthacenecarboxamide dihydrochloride | 2 | N-Heptylamine | 2 hr. | 628(M+H) |
| 15 | [4S-(4alpha,12aalpha)]-4,7-Bis(dimethyl-amino)-1,4,4a,5,5a,6,11,12a-octahydro-3,10,12,12a-tetrahydroxy-1,11-dioxo-9-[[(undecylamino)acetyl]amino]-2-naphthacenecarboxamide dihydrochloride | 2 | Undecylamine | 3.5 hr. | 684(M+H) |
| 16 | [4S-(4alpha,12aalpha)]-4,7-Bis(dimethyl-amino)-1,4,4a,5,5a,6,11,12a-octahydro-3,10,12,12a-tetrahydroxy-1,11-dioxo-9-[[[(2-pyridinylmethyl)amino]acetyl]amido]-2-naphthacenecarboxamide dihydrochloride | 2 | 2-(Aminomethyl) pyridine | 1.5 hr. | 621(M+H) |

EXAMPLE 17

[4S-(4alpha,12aalpha)]-4,7-Bis(dimethylamino)-1,4,4a,5,5a,6,11,12a-octaheydro-3,10,12,12a-tetrahydroxy-9-[[[(2-hydroxyethyl)amino]acetyl]amino1,11-dioxo-2-naphthacenecarboxamide monohydrochloride To a solution of 0.10 g of product from Example 7A in 2 ml of 1,3-dimethyl-2-imidazolidinone is added 0.70 ml of 2-amino-1-ethanol. The solution is stirred at room temperature for 20 minutes, added to 100 ml of diethyl ether and the resulting precipitate collected to give 0.055 g of the desired product.

MS(FAB): m/z 574 (M+H).

Substantially following the method described in detail hereinabove in Example 17, the compounds of this invention listed below in Examples 18–24 are prepared.

| Example # | Name | Starting Material Prod. of Exp. | Reactant | Rx Time | MS(FAB): m/z |
|---|---|---|---|---|---|
| 18 | [4S-(4alpha,12aalpha)]-4,7-Bis(dimethylamino)-1,4,4a,5,5a,6,11,12a-octahydro-3,10,12,12a-tetrahydroxy-9-[[[(2-hydroxyethyl)methylamino]acetyl]amino-1,11-dioxo-2-naphthacenecarboxamide | 7A | 4-methylamino-1-butanol | 0.5 hrs. | 588(M+H) |
| 19 | [4S-(4alpha,12aalpha)]-4,7-Bis(dimethylamino)-1,4,4a,5,5a,6,11,12a-octahydro-3,10,12,12a-tetrahydroxy-9-[[[(4-(hydroxybutyl)amino]acetyl]amino]-1,11-dioxo-2-naphthacenecarboxamide | 7A | 4-amino-1-butanol | 0.5 hr. | 602(M+H) |
| 20 | [4S-(4alpha,12aalpha)]-4,7-Bis(dimethylamino)-1,4,4a,5,5a,6,11,12a-octahydro-3,10,12,12a-tetrahydroxy-1,11-dioxo-9-[[[2,2,2-trifluoroethyl)amino]-acetyl]-2-naphthacenecarboxamide | 7A | 2,2,2-trifluoromethylamine | 2 hr. | 612(M+H) |
| 21 | [4S-(4alpha,12aalpha)]-4,7-Bis(dimethylamino)-9-[[[(2-fluoroethyl)amino]acetyl]-amino]-1,4,4a,5,5a,6,11,12a-octahydro-3,10,12,12a-tetrahydroxy-1,11-dioxo-2-naphthacenecarboxamide | 7A | 2-fluoroethylamine | 2 hr. | 576(M+H) |
| 22 | [4S-(4alpha,12aalpha)]-4,7-Bis(dimethylamino)-1,4,4a,5,5a,6,11,12a-octahydro-3,10,12,12a-tetrahydroxy-1,11-dioxo-9-[[[[2-(1-piperidinyl)ethyl]amino]acetyl]-amino]-2-naphthacenecarboxamide | 7A | 1-(2-aminoethyl)pyrrolidine | 2 hr. | 627(M+H) |
| 23 | [4S-(4alpha,12aalpha)]-4,7-Bis(dimethylamino)-1,4,4a,5,5a,6,11,12a-octahydro-3,10,12,12a-tetrahydroxy-9-[[[methyl-2-propynylamino]acetyl]amino]-1,11-dioxo-2-naphthacenecarboxamide | 7A | N-methylpropargylamine | 2 hrs. | 581(M+H) |
| 24 | [4S-(4alpha,12aalpha)]-4,7-Bis(dimethylamino)-1,4,4a,5,5a,6,11,12a-octahydro-3,10,12,12a-tetrahydroxy-1,11-dioxo-9-[[(1-piperidinylamino)acetyl]-amino]-2-naphthacenecarboxamide | 7A | 1-aminopiperidine | 2 hrs. | 613(M+H) |

EXAMPLE 25

[4S-(4-alpha,12aalpha)]-4,7-Bis(dimethylamino)-1,4,4a,5,5a,6,11,12a-octabydro-3,10,12-12 a-tetrahydroxy-1,11-dioxo-9-[[[(phenylmethoxy)amino]acetyl]amino]-2-naphthacenecarboxamide To 0.50 g of O-benzylhydroxylamine and 2.5 ml of 1,3-dimethyl-2-imidazolidinone is added 0.80 g of sodium bicarbonate. The mixture is stirred at room temperature for 2 hours, filtered and the filtrate added to 0.10 g of product from 7A. The reaction solution is stirred at room temperature for 2 hours and then added to 100 ml of diethyl ether. The resulting precipitate is collected and dried to give 0.90 g of the desired product.

MS(FAB): m/z 636 (M+H).

We claim:

1. A method for the treatment or control of bacterial infections in warm-blooded animals which comprises administering to said animal a pharmacologically effective amount of a compound of the formula:

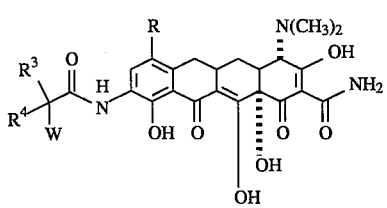

or

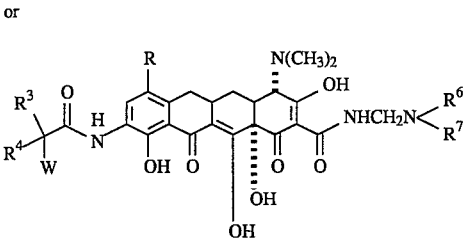

wherein:

R is a halogen selected from bromine, chlorine, fluorine and iodine; or R=—$NR^1R^2$ and $R^1$ is selected from hydrogen, methyl, ethyl, n-propyl, 1-methylethyl, n-butyl or 1-methylpropyl and $R^2$ is selected from methyl, ethyl, n-propyl, 1-methylethyl, n-butyl, 1-methylpropyl, 2-methylpropyl, 1,1-dimethylethyl with the proviso that when R=—$NR^1R^2$ and $R^1$=hydrogen, $R^2$=methyl, ethyl, n-propyl, 1-methyl-ethyl, n-butyl, 1-methylpropyl, 2-methylpropyl or 1,1-dimethylethyl; and when $R^1$=methyl or ethyl, $R^2$=methyl, ethyl, n-propyl, 1-methylethyl, n-butyl, 1-methylpropyl or 2-methylpropyl; and when $R^1$=n-propyl, $R^2$=n-propyl, 1-methylethyl, n-butyl, 1-methylpropyl or 2-methylpropyl; and when $R^1$=1-methylethyl, $R^2$=n-butyl, 1-methylpropyl or 2-methylpropyl; and when $R^1$=n-butyl, $R^2$=n-butyl 1-mthylpropyl or 2-methylpropyl; and when $R^1$=1-methylpropyl, $R^2$=2-methylpropyl;

$R^3$ is selected from hydrogen; straight or branched ($C_4$–$C_8$)alkyl group selected from butyl, isobutyl, pentyl, hexyl, heptyl and octyl; α-mercapto($C_1$–$C_4$)alkyl group selected from mercaptomethyl, α-mercaptoethyl, α-mercapto-1-methylethyl and α-mercaptopropyl; α-hydroxy($C_1$–$C_4$)alkyl group selected from hydroxymethyl, α-hydroxyethyl, α-hydroxy-1-methylethyl and α-hydroxypropyl; carboxyl($C_1$–$C_8$)alkyl group; ($C_6$–$C_{10}$)aryl group selected from phenyl, α-naphyhyl and β-naphthyl; substituted ($C_6$–$C_{10}$)aryl group with substitution selected from hydroxy, halogen, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; ($C_7$–$C_9$)aralkyl group selected from benzyl, 1-phenylethyl, 2-phenylethyl and phenylpropyl; substituted ($C_7$–$C_9$)aralkyl group with substitution selected from halo, ($C_1$–$C_4$)alkyl, nitro, hydroxy, amino, mono- or di-substituted ($C_1$–$C_4$)alkylamino, ($C_1$–$C_4$)alkoxy, ($C_1$–$C_4$)alkylsulfonyl, cyano and carboxy; $R^4$ is selected from hydrogen and ($C_1$–$C_6$)alkyl selected from methyl, ethyl, propyl, isopropyl, butyl, isobutyl, pentyl and hexyl; when $R^3$ does not equal $R^4$ the stereo-chemistry of the carbon bearing the substituent W may be either the racemate (DL) or the individual enatiomers (L or D);

W is selected from hydroxylamino; ($C_7$–$C_{12}$) straight or branched alkyl monosubstituted amino group with substitution selected from heptyl, octyl, nonyl, decyl, undecyl, dodecyl and the diastereomers and enantiomers of said branched alkyl monosubstituted amino group; ($C_1$–$C_4$) straight or branched fluoroalkylamino group selected from trifluoromethylamino, 2,2,2-trifluoroethylamino, 3,3,3-trifluoro-propylamino, 3,3,3,2,2-pentafluoropropylamino, 2,2-difluoropropyl-amino, 4,4,4-trifluorobutylamino and 3,3-difluorobutylamino; ($C_3$–$C_8$)cycloalkkyl monosubstituted amino group with substitution selected from cyclopropyl, trans-1,2-dimethylcyclopropyl, cis1,2-dimethylcyclopropyl, cyclobutyl, cyclopentyl, cyclohexyl, cycloheptyl, cyclooctyl, bicyclo[2.2.1]hept-2-yl, bicyclo[2.2.2]oct-2-yl and the diastereomers and enatiomers of said ($C_3$–$C_8$)cycloalkyl monosubstituted amino group; [($C_4$–$C_{10}$)cycloalkyl]alkyl monosubstituted amino group with substitution selected from (cyclopropyl)methyl, (cyclopropyl)ethyl, (cycobutyl)methyl, (trans-2-methylcyclopropyl)-methyl, and (cis-2-methylcyclobutyl)methyl; ($C_3$–$C_{10}$)alkenyl and alkynyl monosubstituted amino group with substitution selected from allyl, 3-butenyl, 2-butenyl (cis or trans), 2-pentenyl, propynyl, 4-octenyl, 2,3-dimethyl-2-butenyl, 3-methyl-2-butenyl, 2-cyclopentenyl and 2-cyclohexenyl; ($C_6$–$C_{10}$)aryl monosubstituted amino group with substitution selected from phenyl and naphthyl; ($C_7$–$C_{10}$)aralkylamino group selected from benzylamino, 2-phenylethylamino, 1-phenylethylamino 2-(naphthyl)-methylamino, 1-(naphthyl)methylamino and phenylpropylamino; substituted ($C_6$–$C_{10}$)aryl monosubstituted amino group with substitution for the ($C_6$–$C_{10}$)aryl group selected from ($C_1$–$C_5$)acyl, ($C_1$–$C_5$)acylamino, ($C_1$–$C_4$)alkyl, mono or disubstituted ($C_1$–$C_8$)alkylamino, ($C_1$–$C_4$)alkoxy, ($C_1$–$C_4$)alkoxycarbonyl, ($C_1$–$C_4$)alkylsulfonyl, amino, carboxy, cyano, halogen, hydroxy, nitro and trihalo ($C_1$–$C_3$)alkyl; straight or branched symmetrical disubstituted ($C_6$–$C_{14}$)alkylamino group with substitution selected from dibutyl, diisobutyl, di-s-butyl, dipentyl, diisopentyl, di-s-pentyl, dihexyl, diisohexyl and di-s-hexyl; symmetrical disubstituted ($C_6$–$C_{14}$)cycloalkylamino group with substitution selected from dicyclopropyl, dicyclobutyl, dicyclopentyl, di(dicyclopropyl)methyl, dicyclohexyl and dicycloheptyl; straight or branched unsymmetrical di-substituted ($C_3$–$C_{14}$)alkylamino group wherein the total number of carbons in the substitution is no more than 14; unsymmetrical disubstituted ($C_4$–$C_{14}$)cycloalkylamino group wherein the total number of carbons in the substitution is no more than 14; ($C_2$–$C_8$)azacycloalkyl and substituted ($C_2$–$C_8$)azacycloalkyl group selected from 4-methylpiperidine, 4-hydroxypiperidine, 4-(hydroxymethyl)piperidine, 4-(aminomethyl)piperidine, cis-3,4-dimethylpyrrolidinyl, trans-3,4-dimethyl-pyrrolidinyl, 2-azabicyclo[2.1.1]hex2-yl, 5-azabicyclo[2.1.1]hex-5-yl, 2-azabicyclo[2.2.1]hept-2-yl, 7-azabicyclo[2.2.1]hept-7-yl, 2-azabicyclo[2.2.2]oct-2-yl and the diastereomers and enantiomers of said ($C_2$–$C_8$)azacycloalkyl and substituted ($C_2$–$C_8$)azacycloalkyl group; substituted 1-azaoxacycloalkyl group selected from 2-($C_1$–$C_3$)alkylmorpholinyl, 3-($C_1$–$C_3$)alkylisoxazolidinyl, tetrahydroox-azinyl and 3,4-dihydrooxazinyl; [1,n]-diazacycloalkyl and substituted [1,n]-diazacycloalkyl group selected from piperazinyl, 2-($C_1$–$C_3$)alkylpiperazinyl, 4-($C_1$–$C_3$)alkylpiperazinyl, 2,4-dimethylpiperazinyl, 4-($C_1$–$C_4$)alkoxypiperazinyl, 4-($C_6$–$C_{10}$)aryloxypiperazinyl, 4-hydroxypiperazinyl, 2,5-diazabicyclo[2.2.1]hept-2-yl, 2,5-diaza-5-methylbicyclo[2.2.1]hept-2-yl, 2,3-diaza-3-methylbicyclo[2.2.2]oct-2-yl, 2,5-diaza-5,7-dimethylbicyclo[2.2.2]oct-2yl and the diastereomers or enantiomers of said [1,n]-diazacycloalkyl and substituted [1,n]diazacycloalkyl group, 1-azathiacycloalkyl and substituted 1-azathiacycloalkyl group selected from thiomorpholinyl, 2-($C_1$–$C_3$)alkylthiomorpholinyl and 3-($C_3$–$C_6$)cycloalkylthiomorpholinyl; N-azolyl and substituted N-azolyl group selected from 1-imidazolyl, 2-($C_1$–$C_3$)alkyl-1-imidazolyl, 3-($C_1$–$C_3$)alkyl-1-imidazolyl, 1pyrrolyl, 2-($C_1$–$C_3$)alkyl-1-pyrrolyl, 3-($C_1$–$C_3$)alkyl-1-pyrrolyl, 1-pyrazolyl, 3-($C_1$–$C_3$)alkyl-1-pyrazolyl, indolyl, 1-(1,2,3-trizaolyl), 4-($C_1$–$C_3$)alkyl-1 (1,2,3-triazolyl), 5-($C_1$–$C_3$)alkyl-1(1,2,3-triazolyl), 4-(1,2,4-triazolyl), 1-tetrazolyl, 2-tetrazolyl and benzimidazolyl; (heterocycle) amino group and substituted (heterocycle) amino said heterocycle selected from 2- or 3-furanyl, 2- or 3-thienyl, 2-, 3- or 4-pyridyl, 2- or 5-pyridazinyl, 2-pyrazinyl, 2-(imidazolyl), (benzimidazolyl), and (benzothiazolyl) and substitution selected from straight or branched ($C_1$–$C_6$)alkyl; (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl) methylamino, and (benzothiazolyl)methylamino and substituted (heterocycle)methylamino group as defined hereinabove with substitution selected from straight or branched ($C_1$–$C_6$)alkyl; carboxy($C_2$–$C_4$)alkylamino group selected from aminoacetic acid, α-aminopropionic acid, α-aminopropionic acid, α-butyric acid, β-aminobutyric acid and the enantiomers of said carboxy($C_2$–$C_4$)alkkylamino group; 1,1-di-substituted hydrazino group selected from 1,1-dimethylhydrazino, N-aminopiperidinyl, 1,1-diethylhydrazino, and N-aminopyrrolidinyl; ($C_1$–$C_4$)alkoxyamino group selected from methoxyamino, ethoxymino, n-propoxyamino, 1-methylethoxyamino, n-butoxyamino, 2-methylpropoxyamino, and 1,1-dimethylethoxyamino; ($C_3$–$C_8$)cycloalkoxyamino group selected from cyclopropoxyamino, trans-1,2-dimethylcyclopropoxyamino, cis-1,2-dimethylcyclopropoxyamino, cyclobutoxyamino, cyclopentoxyamino, cyclohexoxyamino, cycloheptoxyamino, cyclooctoxyamino, bicyclo [2.2.1] hept-2-yloxyamino, bicyclo[2.2.2]oct-2-yloxy amino and the diastereomers and enantiomers of said ($C_3$–$C_8$)cycloalkoxyamino group; ($C_6$–$C_{10}$)aryloxyamino group selected from phenoxyamino, 1-naphthyloxyamino and 2-naphthyloxyamino; ($C_7$–$C_{11}$)aralalkoxyamino group selected from benzyloxy amino, 2-phenylethoxyamino, 1-phenylethoxyamino, 2-(naphthyl)methoxyamino, 1-(naphthyl)methoxyamino and phenylpropoxyamino; [β or γ-($C_1$–$C_3$)acylamido]alkylamino group selected from 2-(formamido)ethylamino, 2-(acetamido)ethylamino, 2-(propionylamido)ethylamino, 2-(acetamido)propylamino, 2-(formamido)propylamino and the enantiomers of said [β or γ-($C_1$–$C_3$)acylamido]alkylamino group; β or γ-($C_1$–$C_3$)alkoxyalkylamino group selected from 2-methoxethylamino, 2-ethoxyethylamino, 2,2-diethoxyethylamino, 2-methoxypropylamino, 3-methoxypropylamino, 3-ethoxypropylamino, 3,3-diethoxypropylamino and the enantiomers of said β or γ-($C_1$–$C_3$)alkoxyalkylamino group; β, γ, or δ($C_2$–$C_4$)hydroxyalkylamino group selected from 2-hydroxyethylamino, 2-hydroxypropylamino, 3-hydroxypropylamino and 4-hydroxybutylamino;

or $R^3$ and W taken together are selected from —$(CH_2)_n(R^5)N$—, n=3–4, and —$CH_2CH(OH)CH_2(R^5)N$—, wherein $R^5$ is selected from hydrogen and ($C_1$–$C_3$)acyl, the acyl selected from formyl, acetyl, propionyl and ($C_2$–$C_3$)haloacyl selected from chloroacetyl, bromoacetyl, trifluoroacetyl, 3,3,3-trifluoropropionyl and 2,3,2-trifluoropropionyl;

$R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolindinyl, 3-pyrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom selected from γ-butyrolactam, γ-butyrolactone, imidazolidinone or N-aminoimidazolidinone, or a six membered aromatic ring with one to three N heteroatoms selected from pyridyl, pyridazinyl, pyrazinyl, symtriazinyl, unsymtriazinyl, pyrimidinyl or ($C_1$–$C_3$)alkylthiopyridazinyl, or a six membered saturated ring with one or two N, O, S or Se heteroatoms and an adjacent appended O heteroatom selected from 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —$(CH_2)$—$_m COOR^8$ where m=0–4 and $R^8$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, or β-naphthyl;

$R^7$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolidinyl, 3-pyrrolindinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5b]pyridyl or pyridylimidazolyl, or a five membered saturated ring with one or two N, O, S or Se heteroatoms and an adjacent appended O heteroatom selected from γ-butyrolactam, γ-butyrolactone, imidazolidinone or A-aminoimidazolidinone, or a six membered aromatic ring with one to three N heteroatoms selected from pyridyl, pyridazinyl, pyrazinyl, symtriazinyl, unsumtriazinyl, pyrimidinyl or ($C_1$–$C_3$)alkylthiopyridazinyl, or a six membered saturated ring with one or two N, O, S or Se heteroatoms and an adjacent appended O heteroatom selected from 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiiomorpholinyl; or —$(CH_2)$—$_m COOR^8$ where m=0–4 and $R^8$ is selected from hydrogen; straight or branched ($C_1$–$C_3$)alkyl selected from methyl, ethyl, n-propyl or 1-methylethyl; or ($C_6$–$C_{10}$)aryl selected from phenyl, α-naphthyl or β-naphthyl; with the proviso that $R^6$ and $R^7$ cannot both be hydrogen;

or $R^6$ and $R^7$ taken together are —$(CH_2)_2B(CH_2)_2$—, wherein B is selected from $(CH_2)_q$ and q=0–1, —HN, —N($C_1$–$C_3$)alkyl straight or branched, —N($C_1$–$C_4$)alkoxy, oxygen, sulfur or substituted congeners selected from (L or D) proline, ethyl(L or D)prolinate, morpholine, pyrrolidine or piperidine; and the pharmacologically acceptable organic and inorganic salts or metal complexes.

2. A method for the treatment or control of bacterial infections in warm-blooded animals caused by bacteria having the TetM and TetK resistant determinants which comprises administering to said animal a pharmacologically effective amount of a compound:

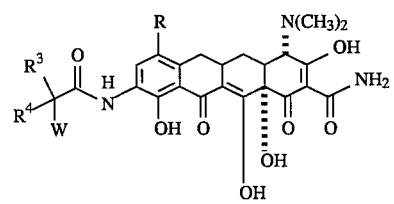

-continued or

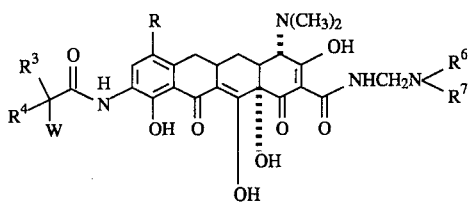

wherein:

R is a halogen selected from bromine, chlorine, fluorine and iodine; or R=—NR$^1$R$^2$ and R$^1$ is selected from hydrogen, methyl, ethyl, n-propyl, 1-methylethyl, n-butyl or 1-methylpropyl and R$^2$ is selected from methyl, ethyl, n-propyl, 1-methylethyl, n-butyl, 1-methylpropyl, 2-methylpropyl, 1,1-dimethylethyl with the proviso that when R=—NR$^1$R$^2$ and R$^1$=hydrogen, R$^2$=methyl, ethyl, n-propyl, 1-methyl-ethyl, n-butyl, 1-methylpropyl, 2-methylpropyl or 1,1-dimethylethyl; and when R$^1$=methyl or ethyl, R$^2$=methyl, ethyl, n-propyl, 1-methylethyl, n-butyl, 1-methylpropyl or 2-methylpropyl; and when R$^1$=n-propyl, R$^2$=n-propyl, 1-methylethyl, n-butyl, 1-methylpropyl or 2-methylpropyl; and when R$^1$=1-methylethyl, R$^2$=n-butyl, 1-methylpropyl or 2-methylpropyl; and when R$^1$=n-butyl, R$^2$=n-butyl, 1-mthylpropyl or 2-methylpropyl; and when R$^1$=1-methylpropyl, R$^2$=2-methylpropyl;

R$^3$ is selected from hydrogen; straight or branched (C$_4$–C$_8$)alkyl group selected from butyl, isobutyl, pentyl, hexyl, heptyl and octyl; α-mercapto(C$_1$–C$_4$)alkyl group selected from mercaptomethyl, α-mercaptoethyl, α-mercapto-1-methylethyl and α-mercaptopropyl; α-hydroxy(C$_1$–C$_4$)alkyl group selected from hydroxymethyl, α-hydroxyethyl, α-hydroxy-1-methylethyl and α-hydroxypropyl; carboxyl(C$_1$–C$_8$)alkyl group; (C$_6$–C$_{10}$)aryl group selected from phenyl, α-naphyhyl and β-naphthyl; substituted (C$_6$–C$_{10}$)aryl group with substitution selected from hydroxy, halogen, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino and carboxy; (C$_7$–C$_9$)aralkyl group selected from benzyl, 1-phenylethyl, 2-phenylethyl and phenylpropyl; substituted (C$_7$–C$_9$)aralkyl group with substitution selected from halo, (C$_1$–C$_4$)alkyl, nitro, hydroxy, amino, mono- or di-substituted (C$_1$–C$_4$)alkylamino, (C$_1$–C$_4$)alkoxy, (C$_1$–C$_4$)alkylsulfonyl, cyano and carboxy;

R$^4$ is selected from hydrogen and (C$_1$–C$_6$)alkyl selected from methyl, ethyl, propyl, isopropyl, butyl, isobutyl, pentyl and hexyl; when R$^3$ does not equal R$^4$ the stereo-chemistry of the carbon bearing the substituent W may be either the racemate (DL) or the individual enatiomers (L or D);

W is selected from hydroxylamino; (C$_7$–C$_{12}$) straight or branched alkyl monosubstituted amino group with substitution selected from heptyl, octyl, nonyl, decyl, undecyl, dodecyl and the diastereomers and enantiomers of said branched alkyl monosubstituted amino group; (C$_1$–C$_4$) straight or branched fluoroalkylamino group selected from trifluoromethylamino, 2,2,2-trifluoroethylamino, 3,3,3-trifluoro-propylamino, 3,3,3,2, 2-pentafluoropropylamino, 2,2-difluoropropyl-amino, 4,4,4-trifluorobutylamino and 3,3-difluorobutylamino;

(C$_3$–C$_8$)cycloalkyl monosubstituted amino group with substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, bicyclo[2.2.1]hept-2-yl, bicyclo[2.2.2]oct-2-yl and the diastereomers and enatiomers of said (C$_3$–C$_8$)cycloalkyl monosubstituted amino group; [(C$_4$–C$_{10}$)cycloalkyl]alkyl monosubstituted amino group with substitution selected from (cyclopropyl)methyl, (cyclopropyl)ethyl, (cycobutyl)methyl, (trans-2-methylcyclopropyl)-methyl, and (cis-2-methylcyclobutyl)methyl; (C$_3$–C$_{10}$)alkenyl and alkynyl monosubstituted amino group with substitution selected from allyl, 3-butenyl, 2-butenyl (cis or trans), 2-pentenyl, propynyl, 4-octenyl, 2,3-dimethyl-2-butenyl, 3-methyl-2-butenyl, 2-cyclopentenyl and 2-cyclohexenyl; (C$_6$–C$_{10}$)aryl monosubstituted amino group with substitution selected from phenyl and naphthyl; (C$_7$–C$_{10}$)aralkylamino group selected from benzylamino, 2-phenylethylamino, 1-phenylethylamino 2-(naphthyl)-methylamino, 1-(naphthyl)methylamino and phenylpropylamino; substituted (C$_6$–C$_{10}$)aryl monosubstituted amino group with substitution for the (C$_6$–C$_{10}$)aryl group selected from (C$_1$–C$_5$)acyl, (C$_1$–C$_5$)acylamino, (C$_1$–C$_4$)alkyl, mono or disubstituted (C$_1$–C$_8$)alkylamino, (C$_1$–C$_4$)alkoxy, (C$_1$–C$_4$)alkoxycarbonyl, (C$_1$–C$_4$)alkylsulfonyl, amino, carboxy, cyano, halogen, hydroxy, nitro and trihalo (C$_1$–C$_3$)alkyl; straight or branched symmetrical disubstituted (C$_6$–C$_{14}$)alkylamino group with substitution selected from dibutyl, diisobutyl, di-s-butyl, dipentyl, diisopentyl, di-s-pentyl, dihexyl, diisohexyl and di-s-hexyl; symmetrical disubstituted (C$_6$–C$_{14}$)cycloalkylamino group with substitution selected from dicyclopropyl, dicyclobutyl, dicyclopentyl, di(dicyclopropyl)methyl, dicyclohexyl and dicycloheptyl; straight or branched unsymmetrical di-substituted (C$_3$–C$_{14}$)alkylamino group wherein the total number of carbons in the substitution is no more than 14; unsymmetrical disubstituted (C$_4$–C$_{14}$)cycloalkylamino group wherein the total number of carbons in the substitution is no more than 14; (C$_2$–C$_8$)azacycloalkyl and substituted (C$_2$–C$_8$)azacycloalkyl group selected from 4-methylpiperidine, 4-hydroxypiperidine, 4-(hydroxymethyl)piperidine, 4-(aminomethyl)piperidine, cis-3,4-dimethylpyrrolidinyl, trans-3,4-dimethyl-pyrrolidinyl, 2-azabicyclo[2.1.1]hex2-yl, 5-azabicyclo[2.1.1]hex-5-yl, 2-azabicyclo[2.2.1]hept-2-yl, 7-azabicyclo[2.2.1] hept-7-yl, 2-azabicyclo[2.2.2]oct-2-yl and the diastereomers and enantiomers of said (C$_2$–C$_8$)azacycloalkyl and substituted (C$_2$–C$_8$)azacycloalkyl group; substituted 1-azaoxacycloalkyl group selected from 2-(C$_1$–C$_3$)alkylmorpholinyl, 3-(C$_1$–C$_3$)alkylisoxazolidinyl, tetrahydroox-azinyl and 3,4-dihydrooxazinyl; [1,n]-diazacycloalkyl and substituted [1,n]-diazacycloalkyl group selected from piperazinyl, 2-(C$_1$–C$_3$)alkylpiperazinyl, 4-(C$_1$–C$_3$)alkylpiperazinyl, 2,4-dimethylpiperazinyl, 4-(C$_1$–C$_4$)alkoxypiperazinyl, 4-(C$_6$–C$_{10}$)aryloxypiperazinyl, 4-hydroxypiperazinyl, 2,5-diazabicyclo[2.2.1]hept-2-yl, 2,5-diaza-5-methylbicyclo[2.2.1]hept-2-yl, 2,3-diaza-3-methylbicyclo[2.2.2]oct-2-yl, 2,5-diaza-5,7-dimethylbicyclo[2.2.2]oct-2yl and the diastereomers or enantiomers of said [1,n]-diazacycloalkyl and substituted [1,n]diazacycloalkyl group, 1-azathiacycloalkyl and substituted 1-azathiacycloalkyl group selected from thiomorpholinyl, 2-($C_1$–$C_3$)alkylthiomorpholinyl and 3-($C_3$–$C_6$)cycloalkylthiomorpholinyl; N-azolyl and substituted N-azolyl group selected from 1-imidazolyl, 2-($C_1$–$C_3$)alkyl-1-imidazolyl, 3-($C_1$–$C_3$)alkyl-1-imidazolyl, 1-pyrrolyl, 2-($C_1$–$C_3$)alkyl-1-pyrrolyl, 3-($C_1$–$C_3$)alkyl-1-pyrrolyl, 1-pyrazolyl, 3-($C_1$–$C_3$)alkyl-1-pyrazolyl, indolyl, 1-(1,2,3-trizaolyl), 4-($C_1$–$C_3$)alkyl-1 (1,2,3-triazolyl), 5-($C_1$–$C_3$)alkyl-1(1,2,3-triazolyl), 4-(1,2,4-triazolyl), 1-tetrazolyl, 2-tetrazolyl and benzimidazolyl; (heterocycle) amino group and substituted (heterocycle) amino said heterocycle selected from 2- or 3-furanyl, 2- or 3-thienyl, 2-,3- or 4-pyridyl, 2- or 5-pyridazinyl, 2-pyrazinyl, 2-(imidazolyl), (benzimidazolyl), and (benzothiazolyl) and substitution selected from straight or branched ($C_1$–$C_6$)alkyl; (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)methylamino group as defined hereinabove with substitution selected from straight or branched ($C_1$–$C_6$)alkyl; carboxy($C_2$–$C_4$)alkylamino group selected from aminoacetic acid, α-aminopropionic acid, β-aminopropionic acid, α-butyric acid, β-aminobutyric acid and the enantiomers of said carboxy($C_2$–$C_4$)alkkylamino group; 1,1-di-substituted hydrazino group selected from 1,1-dimethylhydrazino, N-aminopiperidinyl, 1,1-diethylhydrazino, and N-aminopyrrolidinyl; ($C_1$–$C_4$)alkoxyamino group selected from methoxyamino, ethoxymino, n-propoxyamino, 1-methylethoxyamino, n-butoxyamino, 2-methylpropoxyamino, and 1,1-dimethylethoxyamino; ($C_3$–$C_8$)cycloalkoxyamino group selected from cyclopropoxyamino, trans-1,2-dimethylcyclopropoxyamino, cis-1,2-dimethylcyclopropoxyamino, cyclobutoxyamino, cyclopentoxyamino, cyclohexoxyamino, cycloheptoxyamino, cyclooctoxyamino, bicyclo[2.2.1] hept-2-yloxyamino, bicyclo[2.2.2]oct-2-yloxy amino and the diastereomers and enantiomers of said ($C_3$–$C_8$)cycloalkoxyamino group; ($C_6$–$C_{10}$)aryloxyamino group selected from phenoxyamino, 1-naphthyloxyamino and 2-naphthyloxyamino; ($C_7$–$C_{11}$)aralalkoxyamino group selected from benzyloxy amino, 2-phenylethoxyamino, 1-phenylethoxyamino, 2-(naphthyl)methoxyamino, 1-(naphthyl)methoxyamino and phenylpropoxyamino; [β or γ-($C_1$–$C_3$)acylamido]alkylamino group selected from 2-(formamido)ethylamino, 2-(acetamido)ethylamino, 2-(propionylamido)ethylamino, 2-(acetamido)propylamino, 2-(formamido)propylamino and the enantiomers of said [β or γ-($C_1$–$C_3$)acylamido]alkylamino group; β or γ-($C_1$–$C_3$)alkoxyalkylamino group selected from 2-methoxethylamino, 2- ethoxyethylamino, 2,2-diethoxyethylamino, 2-methoxypropylamino, 3-methoxypropylamino, 3-ethoxypropylamino, 3,3-diethoxypropylamino and the enantiomers of said β or γ-($C_1$–$C_3$)alkoxyalkylamino group; β, γ, or δ($C_2$–$C_4$)hydroxyalkylamino group selected from 2-hydroxyethylamino, 2-hydroxypropylamino, 3-hydroxypropylamino and 4-hydroxybutylamino;

or $R^3$ and W taken together are selected from —($CH_2$)$_n$($R^5$)N—, n=3– 4, and —$CH_2$C—H(OH)$CH_2$($R^5$)N—, wherein $R^5$ is selected from hydrogen and ($C_1$–$C_3$)acyl, the acyl selected from formyl, acetyl, propionyl and ($C_2$–$C_3$)haloacyl selected from chloroacetyl, bromoacetyl, trifluoroacetyl, 3,3,3-trifluoropropionyl and 2,3,2-trifluoropropionyl;

$R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolindinyl, 3-pyrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom selected from γ-butyrolactam, γ-butyrolactone, imidazolidinone or N-aminoimidazolidinone, or a six membered aromatic ring with one to three N heteroatoms selected from pyridyl, pyridazinyl, pyrazinyl, symtriazinyl, unsymtriazinyl, pyrimidinyl or ($C_1$–$C_3$)alkylthiopyridazinyl, or a six membered saturated ring with one or two N, O, S or Se heteroatoms and an adjacent appended O heteroatom selected from 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —($CH_2$)—$_m$COOR$^8$ where m=0–4 and $R^8$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, or β-naphthyl;

$R^7$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolidinyl, 3-pyrrolindinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom selected from γ-butyrolactam, γ-butyrolactone, imidazolidinone or A-aminoimidazolidinone, or a six membered aromatic ring with one to three N heteroatoms selected from pyridyl, pyridazinyl, pyrazinyl, symtriazinyl, unsymtriazinyl, pyrimidinyl or ($C_1$–$C_3$)alkylthiopyridazinyl, or a six membered saturated ring with one or two N, O, S or Se heteroatoms and an adjacent appended 0 heteroatom selected from 2,3-dioxo-1-piperazinyl, 4-ethyl-2,3-dioxo-1-piperazinyl, 4-methyl-2,3-dioxo1-piperazinyl, 4-cyclopropyl-2-dioxo-1-piperazinyl, 2-dioxomorpholinyl, 2-dioxothiiomorpholinyl; or —$(CH_2)$—$_m COOR^8$ where m=0–4 and $R^8$ is selected from hydrogen; straight or branched ($C_1$–$C_3$)alkyl selected from methyl, ethyl, n-propyl or 1-methylethyl; or ($C_6$–$C_{10}$)aryl selected from phenyl, α-naphthyl or β-naphthyl; with the proviso that $R^6$ and $R^7$ cannot both be hydrogen;

or $R^6$ and $R^7$ taken together are —$(CH_2)_2 B(CH_2)_2$—, wherein B is selected from $(CH_2)_q$ and q=0–1, —HN, —N($C_1$–$C_3$)alkyl straight or branched, —N($C_1$–$C_4$)alkoxy, oxygen, sulfur or substituted congeners selected from (L or D) proline, ethyl(L or D)prolinate, morpholine, pyrrolidine or piperidine; and the pharmacologically acceptable organic and inorganic salts or metal complexes.

* * * * *

UNITED STATES PATENT AND TRADEMARK OFFICE
CERTIFICATE OF CORRECTION

PATENT NO. : 5,466,684
DATED : November 14, 1995
INVENTOR(S) : Phaik-Eng Sum, et al It is certified that error appears in the above-indentified patent and that said Letters Patent is hereby corrected as shown below:

In Claim 1, column 32, line 65 of the patent:

Delete "butyl, $R^2$=n-butyl 1-mthylpropyl or ..." and insert "butyl, $R^2$=n-butyl 1-methylpropyl or ..." therefor.

In Claim 1, column 34, line 40 of the patent:

Delete "imidazolyl, 1pyrrolyl, 2-($C_1$-$C_3$)alkyl-1-pyrrolyl," and insert "imidazolyl, 1-pyrrolyl, 2-($C_1$-$C_3$)alkyl-1-pyrrolyl," therefor.

In Claim 1, column 34, line 61 of the patent:

Delete "...onic acid, $\alpha$-aminopropionic acid,..." and insert "...onic acid, $\beta$-aminopropionic acid,..." therefor.

In Claim 2, column 37, line 29 of the patent:

Delete "butyl, $R^2$=n-butyl, 1-mthylpropyl or..." and insert "butyl, $R^2$=n-butyl, 1-methylpropyl or..." therefor.

Signed and Sealed this

Twelfth Day of March, 1996

Attest:

BRUCE LEHMAN

*Attesting Officer*   *Commissioner of Patents and Trademarks*